US007355069B2

(12) United States Patent
Li

(10) Patent No.: US 7,355,069 B2
(45) Date of Patent: Apr. 8, 2008

(54) ORTHO-SUBSTITUTED BENZOIC ACID DERIVATIVES FOR THE TREATMENT OF INSULIN RESISTANCE

(75) Inventor: Lanna Li, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 287 days.

(21) Appl. No.: 10/518,007

(22) PCT Filed: Jun. 17, 2003

(86) PCT No.: PCT/GB03/02584

§ 371 (c)(1),
(2), (4) Date: Dec. 14, 2004

(87) PCT Pub. No.: WO04/000790

PCT Pub. Date: Dec. 31, 2003

(65) Prior Publication Data

US 2005/0256198 A1    Nov. 17, 2005

(30) Foreign Application Priority Data

| Jun. 20, 2002 | (SE) | ................................. | 0201935 |
| Dec. 20, 2002 | (SE) | ................................. | 0203826 |

(51) Int. Cl.
C07C 229/00 (2006.01)
C07C 321/00 (2006.01)
C07C 323/00 (2006.01)
C07C 381/00 (2006.01)
A61K 31/195 (2006.01)

(52) U.S. Cl. ...................... 562/432; 562/450; 514/562; 514/563

(58) Field of Classification Search .................... None
See application file for complete search history.

(56) References Cited

U.S. PATENT DOCUMENTS

| 4,113,871 A | 9/1978 | Stach et al. .................. 424/272 |
| 5,750,783 A | 5/1998 | Goldmann et al. .......... 564/166 |
| 6,258,850 B1 | 7/2001 | Andersson .................... 514/171 |
| 6,306,854 B1 | 10/2001 | Brown et al. ............ 514/237.8 |
| 6,906,058 B2 | 6/2005 | Starke et al. ........... 514/211.01 |
| 7,125,864 B2 | 10/2006 | Starke et al. ........... 514/211.09 |
| 7,132,416 B2 | 11/2006 | Starke et al. ........... 514/211.08 |
| 7,192,945 B2 | 3/2007 | Starke et al. ........... 514/211.09 |
| 7,192,946 B2 | 3/2007 | Starke et al. ........... 514/211.09 |
| 7,192,947 B2 | 3/2007 | Starke et al. ........... 514/211.09 |
| 7,226,943 B2 | 6/2007 | Starke et al. ............... 514/431 |
| 7,238,684 B2 | 7/2007 | Starke et al. ........... 514/211.08 |
| 2002/0022656 A1 | 2/2002 | Per Sauerberg et al. .... 514/553 |
| 2005/0222261 A1 | 10/2005 | Li .............................. 514/563 |
| 2005/0267149 A1 | 12/2005 | Li .............................. 514/307 |

FOREIGN PATENT DOCUMENTS

EP    0 802 186 A    10/1997

| EP | 1 184 366 A | 3/2002 |
| WO | 99/20275 | 4/1999 |
| WO | 99/32477 | 7/1999 |
| WO | 00/64876 | 11/2000 |
| WO | 00/64888 | 11/2000 |
| WO | 01/12187 A2 | 2/2001 |
| WO | WO 01/66533 | 9/2001 |
| WO | WO 02/32428 | 4/2002 |
| WO | WO 02/50051 | 6/2002 |
| WO | WO 03/020710 | 3/2003 |
| WO | WO 03/022286 | 3/2003 |
| WO | WO 03/022825 | 3/2003 |
| WO | WO 03/022830 | 3/2003 |
| WO | WO 03/05821 | 6/2003 |
| WO | WO 03/051822 | 6/2003 |
| WO | WO 03/051826 | 6/2003 |
| WO | WO 03/091232 | 11/2003 |
| WO | 2004/000294 A1 | 12/2003 |
| WO | 2004/000295 A1 | 12/2003 |
| WO | WO 03/106482 | 12/2003 |
| WO | WO 04/000294 | 12/2003 |
| WO | WO 04/000295 | 12/2003 |
| WO | WO 04/056748 | 6/2004 |
| WO | WO 04/110984 | 12/2004 |
| WO | WO 04/110985 | 12/2004 |
| WO | WO 04/113276 | 12/2004 |
| WO | WO 04/113282 | 12/2004 |
| WO | WO 04/113283 | 12/2004 |
| WO | WO 04/113284 | 12/2004 |
| WO | WO 04/113285 | 12/2004 |

*Primary Examiner*—Sikarl A. Witherspoon
(74) *Attorney, Agent, or Firm*—Morgan, Lewis & Bockius LLP

(57) ABSTRACT

The present invention provides a compound of formula (I), wherein n is 0, 1 or 2 and $R^1$ represents halo, a $C_{1-4}$alkyl group which is optionally substituted by one or more fluoro, a $C_{1-4}$alkoxy group which is optionally substituted by one or more fluoro and wherein when n is 2 the substituents $R^1$ may be the same or different; $R^2$ represents a $C_{2-8}$alkyl group which is optionally interrupted by oxygen; Y is absent or represents methylene; and X is O or S; and pharmaceutically acceptable salts and prodrugs thereof, to processes for preparing such compounds, to their utility in treating clinical conditions associated with insulin resistance, to methods for their therapeutic use and to pharmaceutical compositions containing them (I)

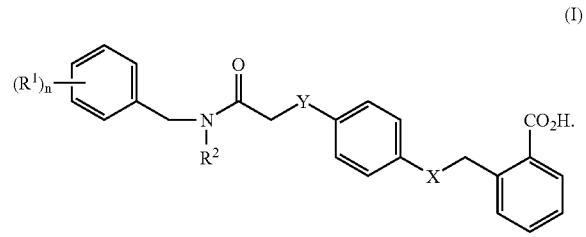

27 Claims, No Drawings

ORTHO-SUBSTITUTED BENZOIC ACID DERIVATIVES FOR THE TREATMENT OF INSULIN RESISTANCE

FIELD OF THE INVENTION

The present invention relates to certain novel benzoic acid derivatives, to processes for preparing such compounds, to their utility in treating clinical conditions associated with insulin resistance, to methods for their therapeutic use and to pharmaceutical compositions containing them.

BACKGROUND OF THE INVENTION

The Insulin Resistance Syndrome (IRS) including type 2 diabetes mellitus, which refers to a cluster of manifestations including insulin resistance with accompanying hyperinsulinaemia, possible type 2 diabetes mellitus, arterial hypertension, central (visceral) obesity, dyslipidaemia observed as deranged lipoprotein levels typically is characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in IRS suffering patients and thus to correct the dyslipidaemia which is considered to cause the accelerated progress of atherosclerosis. However, currently this is not a universally well defined disease.

Modulators of peroxisome proliferator-activated receptors (PPAR, for a review of the PPARs see T. M. Willson et al, J Med Chem 2000, Vol 43, 527) are effective in treating conditions associated with insulin resistance.

U.S. Pat. No. 5,750,783 discloses that certain benzyloxy-substituted phenylglycinolamides which have a cycloalkyl substituent are antiatherosclerotic medicaments. This document does not disclose or suggest the compounds of the present invention. Surprisingly a series of compounds has now been found which are selective PPARα modulators.

DESCRIPTION OF THE INVENTION

The present invention provides a compound of formula I

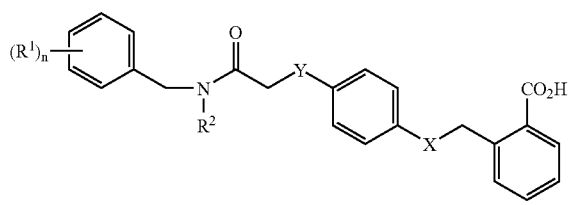

wherein n is 0, 1 or 2 and $R^1$ represents halo, a $C_{1-4}$alkyl group which is optionally substituted by one or more fluoro, a $C_{1-4}$alkoxy group which is optionally substituted by one or more fluoro and wherein when n is 2 the substituents $R^1$ may be the same or different;

$R^2$ represents a $C_{2-8}$alkyl group which is optionally interrupted by oxygen;
Y is absent or represents methylene; and
X is O or S;
and pharmaceutically acceptable salts and prodrugs thereof.

Further values of $R^1$, $R^2$, Y and X in compounds of Formula I now follow. It will be understood that such values may be used where appropriate with any of the definitions, claims or embodiments defined hereinbefore or hereinafter.

In one aspect X is O.
In a second aspect X is S.
In a third aspect Y is methylene.
In a fourth aspect Y is absent.
In a fifth aspect $R^1$ is halo, a $C_{1-4}$alkyl group or a $C_{1-4}$alkoxy group and n is 0, 1 or 2.
Particularly $R^1$ is fluoro, methoxy, or isopropyl when n is 1 or 2. Particularly n is 0.
In a sixth aspect $R^2$ represents a $C_{5-7}$alkyl group.

The term $C_{2-8}$alkyl denotes a straight-chain or branched saturated aliphatic hydrocarbon having from 2 to 8 carbon atoms. Examples of said alkyl include ethyl, n-propyl, iso-propyl, n-butyl, iso-butyl, sec-butyl, t-butyl and straight- and branched-chain pentyl, hexyl, heptyl and octyl.

It will be understood by those skilled in the art that the term interrupted as used above means that the oxygen atom is situated within the alkyl chain and is not the terminal atom. The term "prodrug" as used in this specification includes derivatives of the carboxylic acid group which are converted in a mammal, particularly a human, into the carboxylic acid group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy are known in the art. For examples of such prodrug derivatives, see:

a) Design of Prodrugs, edited by H. Bundgaard, (Elsevier, 1985) and Methods in Enzymology. 42: 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8:1-38 (1992);
d) H. Bundgaard, et al., Journal of Pharmaceutical Sciences, 77:285 (1988); and
e) N. Kalceya, et al., Chem Pharm Bull, 32:692 (1984).

The above documents a to e are herein incorporated by reference.

In vivo cleavable esters are just one type of prodrug of the parent molecule.

The compounds of formula I have activity as medicaments, in particular the compounds of formula I are selective agonists of PPARα, that is, their $EC_{50}$ for PPARα is at least three times lower, preferably at least four times lower and more preferably 10 or 50 times lower than their respective $EC_{50}$ for PPARγ wherein the $EC_{50}$s are measured and calculated as described in the assays later in this document. The compounds of formula I are potent and selective.

Specific compounds of the invention are one or more of the following:
2-[(4-{3-[benzyl(hexyl)amino]-3-oxopropyl}phenoxy)methyl]benzoic acid;

2-{[(4-{2-[(2,4-difluorobenzyl)(heptyl)amino]-2-oxoethyl}phenyl)thio]methyl}benzoic acid;
2-[(4-{2-[benzyl(hexyl)amino]-2-oxoethyl}phenoxy)methyl]benzoic acid;
2-[(4-{2-[(2,4-difluorobenzyl)(heptyl)amino]-2-oxoethyl}phenoxy)methyl]benzoic acid;
2-[(4-{3-[(2,4-difluorobenzyl)(heptyl)amino]-3-oxopropyl}phenoxy)methyl]benzoic acid;
2-{[(4-{3-[(2,4-difluorobenzyl)(heptyl)amino]-3-oxopropyl}phenyl)thio]methyl}benzoic acid;
2-[(4-{3-[butyl(2,3-dimethoxybenzyl)amino]-3-oxopropyl}phenoxy)methyl]benzoic acid;
2-[(4-{3-[(2,3-dimethoxybenzyl)(heptyl)-amino]-3-oxopropyl}phenoxy)methyl]benzoic acid;
2-[(4-{3-[(3-ethoxypropyl)(4-isopropylbenzyl)amino]-3-oxopropyl}phenoxy)methyl]-benzoic acid;
2-[(4-{3-[(2,4-difluorobenzyl)(propyl)amino]-3-oxopropyl}phenoxy)methyl]benzoic acid;
2-[(4-{2-[ethyl(2-fluorobenzyl)amino]-2-oxoethyl}phenoxy)methyl]benzoic acid;
2-[(4-{3-[ethyl(2-fluorobenzyl)amino]-3-oxopropyl}phenoxy)methyl]benzoic acid;
2-({[4-(2-{ethyl[4-(trifluoromethyl)benzyl]amino}-2-oxoethyl)phenyl]thio}-methyl)benzoic acid;
2-{[(3-{2-[(2,4-difluorobenzyl)(heptyl)amino]-2-oxoethyl}phenyl)thio]methyl}benzoic acid; and
2-{[(4-{2-[(4-chlorobenzyl)(ethyl)amino]-2-oxoethyl}phenyl)thio]methyl}benzoic acid and pharmaceutically acceptable salts thereof.

A second group of specific compounds of the invention comprises a compound selected from:
2-{[(4-{2-[(2,4-difluorobenzyl)(heptyl)amino]-2-oxoethyl}phenyl)thio]methyl}benzoic acid;
2-{[(4-{3-[(2,4-difluorobenzyl)(heptyl)amino]-3-oxopropyl}phenyl)thio]methyl}benzoic acid;
2-({[4-(2-{ethyl[4-(trifluoromethyl)benzyl]amino}-2-oxoethyl)phenyl]thio}-methyl)benzoic acid;
2-{[(3-{2-[(2,4-difluorobenzyl)(heptyl)amino]-2-oxoethyl}phenyl)thio]methyl}benzoic acid; and
2-{[(4-{2-[(4-chlorobenzyl)(ethyl)amino]-2-oxoethyl}phenyl)thio]methyl}benzoic acid and pharmaceutically acceptable salts thereof.

A third group of specific compounds of the invention comprises a compound selected from:
2-[(4-{3-[benzyl(hexyl)amino]-3-oxopropyl}phenoxy)methyl]benzoic acid;
2-[(4-{2-[benzyl(hexyl)amino]-2-oxoethyl}phenoxy)methyl]benzoic acid;
2-[(4-{2-[(2,4-difluorobenzyl)(heptyl)amino]-2-oxoethyl}phenoxy)methyl]benzoic acid;
2-[(4-{3-[(2,4-difluorobenzyl)(heptyl)amino]-3-oxopropyl}phenoxy)methyl]benzoic acid;
2-[(4-{3-[butyl(2,3-dimethoxybenzyl)amino]-3-oxopropyl}phenoxy)methyl]benzoic acid;
2-[(4-{3-[(2,3-dimethoxybenzyl)(heptyl)-amino]-3-oxopropyl}phenoxy)methyl]benzoic acid;
2-[(4-{3-[(3-ethoxypropyl)(4-isopropylbenzyl)amino]-3-oxopropyl}phenoxy)methyl]-benzoic acid;
2-[(4-{3-[(2,4-difluorobenzyl)(propyl)amino]-3-oxopropyl}phenoxy)methyl]benzoic acid;
2-[(4-{2-[ethyl(2-fluorobenzyl)amino]-2-oxoethyl}phenoxy)methyl]benzoic acid;
2-[(4-{3-[ethyl(2-fluorobenzyl)amino]-3-oxopropyl}phenoxy)methyl]benzoic acid;

and pharmaceutically acceptable salts thereof.

Certain compounds of the present invention may exist as tautomers. It is to be understood that the present invention encompasses all such tautomers.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

Methods of Preparation

The compounds of the invention may be prepared as outlined below. However, the invention is not limited to these methods, the compounds may also be prepared as described for structurally related compounds in the prior art. The reactions can be carried out according to standard procedures or as described in the experimental section.

Compounds of formula I may be prepared by reacting a compound of formula II

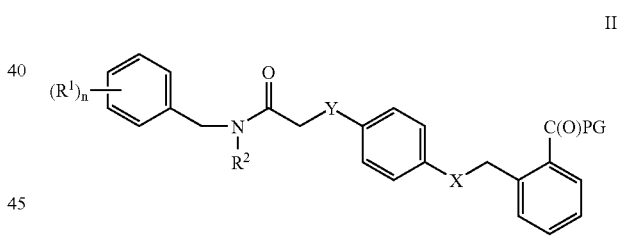

in which $R^1$, $R^2$, X and Y are as previously defined and PG represents a protecting group for a carboxylic hydroxy group as described in the standard text "Protective Groups in Organic Synthesis", $2^{nd}$ Edition (1991) by Greene and Wuts, with a de-protecting agent. The protecting group may also be a resin, such as Wang resin or 2-chlorotrityl chloride resin. Protecting groups may be removed in accordance to techniques which are well known to those skilled in the art. One such protecting group is where PG represents a $C_{1-6}$alkoxy group or an arylalkoxy group eg benzyl, such that COPG represents an ester. Such esters can be reacted with a hydrolysing agent, for example lithium hydroxide in the presence of a solvent for example a mixture of THF and water or potassium hydroxide in a $C_{1-3}$ alcohol for example methanol, at a temperature in the range of 0-200° C. or by microwave radiation to give compounds of formula I.

Compounds of formula II may be prepared by reacting a compound of formula III

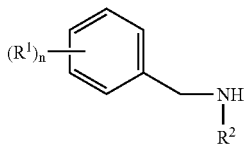

III or a salt thereof, for example a hydrochloride salt, in which $R^1$, $R^2$ and n are as previously defined with a compound of formula IV

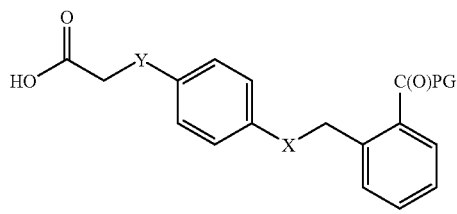

IV or the acid chloride thereof in which X, Y and PG are as previously defined in an inert solvent, for example dichloromethane, optionally in the presence of a coupling agent, for example 4-dimethylaminopyridine or 1-ethyl-3-(3-dimethylaminopropyl)carbodiimide hydrochloride, at a temperature in the range of −25° C. to 150° C.

Compounds of formula II may also be prepared by reacting a compound of formula V

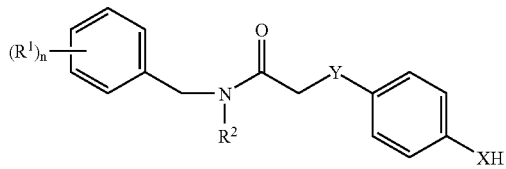

V in which $R^1$, n, $R^2$, X and Y are as previously defined with a compound of formula VI

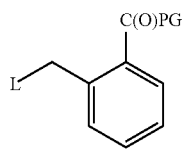

VI in which PG is as previously defined and L represents a leaving group, for example halo, is e.g. bromo, optionally in the presence of solvent, for example acetonitrilie, and optionally in the presence of a base, for example potassium carbonate, at a temperature in the range of 0 to 150° C.

Compounds of formula III, IV, V and VI may be prepared by methods described in the Examples or by analogous methods known to those skilled in the art.

Compounds of formula II, III, IV and V are useful intermediates in the preparation of compounds of formula I. Certain of these compounds are believed to be novel. Novel compounds of formula II, or formula III, or formula IV or formula V are herein claimed as a further aspect of the present invention.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation, where necessary, hydroxy, amino or other reactive groups may be protected using a protecting group, $R^p$ as described in the standard text "Protective groups in Organic Synthesis", $2^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid or as a pharmaceutically acceptable salt, in a pharmaceutically acceptable dosage form. Depending upon the disorder and patient to be treated and the route of administration, the compositions may be administered at varying doses.

Suitable daily doses of the compounds of the invention in therapeutic treatment of humans are about 0.0001-100 mg/kg body weight, preferably 0.001-10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or a pharmaceutically acceptable salt thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt, solvate, solvate of such a salt or a prodrug thereof, may be administered in association with another PPAR modulating agent. PPAR modulating agents include but are not limited to a PPAR alpha and/or gamma and/or delta agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to BMS 298585, clofibrate, fenofibrate, bezafibrate, gemfibrozil and ciprofibrate; GW 9578, pioglitazone, rosiglitazone, rivoglitazone, balaglitazone, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxy-phenyl}ethoxy)phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]-pyrimidin-5-yl] (3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl] (3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or cholestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 94/24087, WO 96/05188, WO 96/08484, WO 96/16051, WO 97/33882, WO98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 01/34570, WO 00/35889, WO 00/47568, WO 00/61568, WO 01/68637, WO 01/68096, WO 02/08211, WO 00/38725, WO 00/38726, WO 00/38727, WO 00/38728, WO 00/38729, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 869 121, EP 864 582, and EP 1 070 703, and the contents of these patent applications, particularly the compounds described in claim 1 and the named examples, are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-α-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl] ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a nicotinic acid derivative, including slow release and combination products, for example, nicotinic acid (niacin), acipimox and niceritrol;

a phytosterol compound for example stanols;

probucol;

an omega-3 fatty acid for example Omacor™;

an anti-obesity compound for example orlistat (EP 129,748) and sibutramine (GB 2,184,122 and U.S. Pat. No. 4,929,629);

an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

aspirin;

a Melanin concentrating hormone (CH) antagonist;

a PDK inhibitor; or modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore in an additional feature of the invention, there is provided a method for for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt, solvate, solvate of such a salt or a prodrug thereof, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt, solvate, solvate of such a salt or a prodrug thereof, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES $^1$H NMR and $^{13}$C NMR measurements were performed on a Varian Mercury 300 or Varian UNITY plus 400, 500 or 600 spectrometers, operating at ¹H frequencies of 300, 400, 500 and 600 MHz, respectively, and at ¹³C frequencies of 75, 100, 125 and 150 MD, respectively. Measurements were made on the delta scale (δ).

Unless otherwise stated, chemical shifts are given in ppm with the solvent as internal standard.

| Abbreviations | |
|---|---|
| IRS | insulin resistance syndrome |
| TLC | thin layer chromatography |
| HOBT | 1-hydroxybenzotriazole-hydrate |
| DIBAH | diisobutylaluminium hydride |
| DMSO | dimethyl sulfoxide |
| EtOAc | ethyl acetate |
| DMF | N,N-dimethylformamide |
| THF | tetrahydrofuran |
| PEG | polyethylene glycol |
| HPLC | high performance liquid chromatography |
| MeCN | acetonitrile |
| TFA | trifluoroacetic acid |
| Pd/C | palladium on charcoal |
| HATU | O-(7-azabenzotriazolyl-1-yl)-N,N,N',N'-tetramethyluronium hexafluorophosphate |
| DCM | dichloromethane |
| TBTU | O-(benzotriazol-1-yl)-N,N,N',N'-tetramethyluronium tetrafluoborate |
| DIPEA | N,N-diisopropylethylamine |
| DMAP | 4-dimethylaminopyridine |
| Trisamine | Tris(hydroxymethyl)aminomethane |
| ISOLUTE ® FLASH Si | is a silica column suitable for chromatography |
| Borohydride on polymer support is Borohydride on Amberlite IRA-400 available from Aldrich | |
| EDC | 1-ethyl-3-(3-dimethylaminopropyl)carbodiimide hydrochloride |
| NH₄OAc | ammonium acetate |
| t | triplet |
| s | singlet |
| d | doublet |
| q | quartet |
| qvint | quintet |
| m | multiplet |
| br | broad |
| bs | broad singlet |
| dm | doublet of multiplet |
| bt | broad triplet |
| dd | doublet of doublet |

Example 1 a) N-benzyl-N-hexyl-3-(4-hydroxyphenyl)propanamide

N-hexylbenzylamine (0.6 g, 3.136 mmol) and 3-(4-hydroxyphenyl)propionic acid (0.52 g 3.136 mmol) were mixed in DMF (10 ml) and the mixture was cooled. HOBT (0.424 g, 3.136 mmol) and the TBTU (1 g, 3.136 mmol) reagent were added followed by DIPEA (1.216 g, 9.409 mmol). The mixture was stirred at room temperature overnight and then evaporated. The resulting mixture was partitioned between ethyl acetate and sodium hydrogencarbonate aqueous solution (sat.). The aqueous portion was extracted with ethyl acetate and the combined organic extracts dried with magnesium sulphate and then evaporated. Chromatography of the residue on a column (ISOLUTE® SI, 5 g/25 ml) using ethyl acetate/heptane (10:90, then 25:75) as eluant gave 760 mg the desired product, yield 71%.

¹H NMR (500 MHz, CDCl₃): δ 0.84 (t, 3H), 1.16-1.27 (m, 6H), 1.41-1.51 (m, 2H), 2.55, 2.63 (t, t, 2H), 2.88, 2.94 (t, t, 2H), 3.09, 3.31 (t, t, 2H), 4.40, 4.57 (s, s, 2H), 6.69, 6.73 (d, d, 2H), 6.98 (d, 2H), 7.05, 7.07 (d, d, 2H), 7.14 (d, 1H) and 7.21-7.31 (m, 5H)

b) Methyl 2-[(4-{3-[benzyl(hexyl)amino]-3-oxopropyl}phenoxy)methyl]benzoate

N-benzyl-N-hexyl-3-(4-hydroxyphenyl)propanamide (183 mg, 0.54 mmol), methyl 2-(bromomethyl)benzoate (136 mg, 0.59 mmol) and potassium carbonate (112 mg, 0.81 mmol) were mixed in acetonitrile. The mixture was stirred at 66° C. overnight. The solvent was evaporated under reduced pressure and the residue was dissolved in ethyl acetate. The organic phase was washed (water ×2, brine ×1), dried (Na₂SO₄) and evaporated. Further purification by preparative HPLC (using a gradient of CH₃CN/10% CH₃CN-waterphase containing 0.1M NH₄OAc as eluant) gave 91 mg (yield 34%) of the desired product.

¹HNMR (rotamers, 400 MHz, CDCl₃): δ 0.84-0.88 (m, 3H), 1.19-1.29 (m, 6H), 1.42-1.53 (m, 2H), 2.57, 2.65 (t, t, 2H), 2.92, 2.99 (t, 2H), 3.10, 3.34 (t, t, 2H), 3.89, 3.90 (s, s, 3H), 4.42, 4.60 (s, s, 2H), 5.47, 5.48 (s, s, 2H), 6.86-6.93 (m, 2H), 7.07 (t, 2H), 7.14-7.19 (m, 2H), 7.21-7.38 (m, 4H), 7.52-7.56 (m, 1H), 7.75 (t, 1H), 8.00-8.03 (m, 1H).

c) 2-[(4-{3-[Benzyl(hexyl)amino]-3-oxopropyl}phenoxy)methyl]benzoic acid

Methyl 2-[(4-{3-[benzyl(hexyl)amino]-3-oxopropyl}phenoxy)methyl]benzoate (61 mg, 0.13 mmol) and lithium hydroxide (7 mg, 0.29 mmol) were dissolved in 3 ml of a 1:1 mixture of THF and water in a microwave vial. The resulting reaction mixture was irradiated in a microwave oven at 120° C. for 40 min.

Water was added and the THF was evaporated under reduced pressure. The residue was acidified with 1M hydrochloric acid and extracted with ethyl acetate (×3). The organic phases were combined, washed (water, brine), dried (Na₂SO₄) and evaporated. The crude product was further purified by preparative HPLC (using a gradient of CH3CN/ 10% CH₃CN-waterphase containing 0.1M NH₄OAc as eluant).

38 mg (yield 64%) of pure product was obtained after freeze-drying.

¹HNMR (rotamers, 400 MHz, CDCl₃): δ 0.86 (t, 3H), 1.19-1.28 (m, 6H), 1.43-1.55 (m, 2H), 2.60, 2.69 (t, t, 2H), 2.92, 2.99 (t, t, 2H), 3.11, 3.36 (t, t, 2H), 4.43, 4.61 (s, s, 2H), 5.52, 5.53 (s, s, 2H), 6.87-6.93 (m, 2H), 7.05-7.09 (m, 2H), 7.14-7.33 (m, 5H), 7.36-7.40 (m, 1H), 7.55-7.59 (m, 1H), 7.77 (t, 1H) and 8.12-8.15 (m, 1H). ¹³CNMR (rotamers, 100 MHz, CDCl₃): δ 14.17, 14.23, 22.73, 22.79, 26.75, 26.88, 27.68, 27.72, 31.11, 31.26, 31.61, 31.82, 35.39, 35.68, 46.84, 47.48, 48.72, 51.35, 68.42, 115.16, 115.22, 126.39, 127.15, 127.42, 127.49, 127.72, 128.23, 128.70, 129.10, 129.72, 131.81, 133.45, 133.81, 133.84, 137.10, 137.82, 140.88, 157.33, 157.40, 171.20, 173.10, 173.39.

Example 2 a) N-(2,4-difluorobenzyl)-N-heptylamine

Heptylamine (345.6 mg, 3 mmol) was added into 2,4-difluorobenzaldehyde (440.5 mg, 3.1 mmol) in MeOH (3 ml) and trimethyl orthoformate (2 ml), followed by acetic acid (0.05 ml). The mixture was in microwave oven (Smith Synthesizer) at 150° C. for 10 minutes. DCM (3 ml) was then added and followed borohydride on polymer support (1.2 g, 3 mmol). The mixture was shaken overnight and more of borohydride on polymer support (1.2 g) was added. The mixture was shaken over weekend and then filtered and evaporated. The residue was put on a column ((ISOLUTE®PRS, 10 g) and eluted with MeCN, MeOH and then MeOH(NH$_3$ sat.). 536 mg of oil product was obtained, yield 72%.

$^1$H NMR (400 MHz, CDCl$_3$): δ 0.87 (t, 3H), 1.23-1.32 (m, 8H), 1.45-1.52 (m, 2H), 2.59 (t, 2H), 3.78 (s, 2H), 6.75-6.85 (m, 2H) and 7.27-7.33 (m, 1H)

b) (4-{[2-(Methoxycarbonyl)benzyl]thio}phenyl) acetic acid

4-Mercaptophenylacetic acid (995 mg, 5.915 mmol) in THF (15 ml) was cooled in an ice-bath and sodium hydride (55-65%, 520 mg, ~13 mmol) was added. The mixture was stirred for 30 minutes and then 2-bromomethyl-benzoic acid methyl ester (1.49 g, 6.507 mmol) in THF (5 ml) was added. The resulting mixture was stirred overnight and the temperature was allowed going up to room temperature. Water was dropped in and the mixture was stirred for ca. 20 minutes. It was then evaporated to remove THF. The residue was acidified with 1% hydrochloric acid, pH~3, and then extracted with ethyl acetate. The organic extracts were combined, dried with magnesium sulphate and evaporated. Chromatography of the residue on a column (ISOLUTE® SI, 20 g/70 ml) using DCM, then MeOH/DCM (1:99) as eluant gave 224 mg desired product, yield 65%.

$^1$H NMR (500 MHz, CDCl$_3$): δ 3.62 (s, 2H), 3.90 (s, 3H), 4.52 (s, 2H), 7.17 (d, 2H), 7.23-7.40 (m, 5H) and 7.94 (d, 1H)).

c) Methyl 2-{[(4-{2-[(2,4-difluorobenzyl)(heptyl)amino]-2-oxoethyl}phenyl)thio]methyl}benzoate (4-{[2-(Methoxycarbonyl)benzyl]thio}phenyl)acetic acid (581 mg, 1.836 mmol) and N-(2,4-difluorobenzyl)-N-heptylamine (465.3 mg, 1.968 mmol) were combined in DMF and the mixture was cooled in an ice-bath. HOBT (260.6 mg, 1.928 mmol) and TBTU (619 mg, 1.928 mmol) were added, followed by DIPEA (747.7 mg 5.785 mmol). The mixture was stirred at room temperature overnight and then evaporated. The resulting mixture was partitioned between ethyl acetate and sodium hydrogencarbonate aqueous solution (sat.). The aqueous portion was extracted with ethyl acetate and the combined organic extracts was dried with magnesium sulphate and then evaporated. Chromatography of the residue on a column (ISOLUTE® SI, 20 g/70 ml) using ethyl acetate/heptane (5:95, then 10:90) as eluant gave 767 mg the desired product, yield 77%.

$^1$H NMR (rotamers, 500 MHz, CDCl$_3$): δ 0.88-0.93 (m, 3H), 1.23-1.34 (m, 8H), 1.48-1.57 (m, 2H), 3.19-3.24, 3.30-3.37 (m, m, 2H), 3.67-3.74 (m, 2H), 3.92 (s, 3H), 4.50, 4.63 (s, s, 2H), 4.53 (s, 2H), 6.78-6.89 (m, 2H), 7.00-7.40 (m, 8H) and 7.95 (d, 2H).

d) 2-{[(4-{2-[(2,4-Difluorobenzyl)(heptyl)amino]-2-oxoethyl}phenyl)thio]methyl}benzoic acid Methyl 2-{[(4-{2-[(2,4-difluorobenzyl)(heptyl)amino]-2-oxoethyl}phenyl)thio]methyl}-benzoate (31 mg, 0.057 mmol) was dissolved in THF (1 ml) and cooled in an ice-bath. Lithium hydroxide (2 mg, 0.075 mmol) in water (1 ml) was added. After the addition, the cooling bath was removed and the mixture was stirred overnight. LC-MS showed there was very little product. More lithium hydroxide (3 mg) was added and the mixture was stirred for 6 days more and HPLC showed about 30% product. More (3 mg) of lithium hydroxide was added and the mixture was stirred for 13 days more. It was evaporated in vacuum to remove THF. The residue was acidified with 10% hydrochloric acid, pH~3, and extracted with ethyl acetate (×2). The organic phases were combined, dried (magnesium sulphate) and evaporated. Chromatography of the residue on a column (ISOLUTE® SI, 500 g/3 ml) using DCM, MeOH/DCM (0.5:99.5) as eluant gave 17 mg desired product, yield 56%.

$^1$H NMR (rotamers, 500 MHz, CDCl$_3$): δ 0.89-0.93 (m, 3H), 1.25-1.34 (m, 8H), 1.52-1.60 (m, 2H), 3.27, 3.37 (t, t, 2H), 3.71, 3.76 (s, s, 2H), 4.55, 4.65 (s, s, 2H), 6.80-6.92 (m, 2H), 7.07-7.17 (m, 2H), 7.28-7.37 (m, 5H), 7.42-7.47 (m, 1H) and 7.95-7.98 (m, 1H). $^{13}$C NMR (rotamers, 125 MHz, CDCl$_3$): δ 14.01, 22.51, 26.78, 26.85, 27.28, 28.56, 28.85, 28.93, 31.65, 31.70, 38.22, 39.94, 40.25, 41.57, 41.60, 45.16, 46.48, 47.94, 103.53 (t), 104.26(t), 111.50(br), 111.71 (br), 119.65(d), 120.37(d), 127.05, 128.95 (br), 129.61, 129.68, 131.15, 131.66(d), 131.76(d), 132.41, 132.80, 132.88, 133.85, 134.03, 140.43, 160.58 (dd), 160.91(dd), 162.21(dd), 162.53(dd), 170.46, 171.44 and 171.54.

Example 3 a) (4-{[2-(Methoxycarbonyl)benzyl]oxy}phenyl) acetic acid

4-Hydroxyphenylacetic acid (760 mg, 4.995 mmol) was dissolved in ethanol (99.5%, 20 ml). Potassium hydroxide (560.5 mg, 9.99 mmol) was added. The mixture was stirred at room temperature for 30 minutes. 2-Bromomethylbenzoic acid methyl ester (1144.2 mg, 4.995 mmol) was then dropped in. The resulting mixture was heated to reflux for 2 hours and then evaporated in vacuum to dry. Water and ethyl acetate were added into the residue and the phases were separated. The water phase was acidified with 10% hydrochloric acid, pH~5, and then extracted with ethyl acetate. The organic phase was dried with magnesium sulphate and evaporated in vacuum to dry. Chromatography of the residue on a column (ISOLUTE® SI, 5 g/6 ml) using DCM, MeOH/DCM (1:99) as eluant gave the desired product (262 mg), yield 17.5%.

$^1$H NMR (500 MHz, CDCl$_3$): δ 3.61 (s, 2H), 3.91 (s, 3H), 5.50 (s, 2H), 6.97 (d, 2H), 7.22 (d, 2H), 7.39 (t, 1H), 7.57 (t, 1H), 7.76 (d, 1H) and 8.04 (d, 1H).

b) Methyl 2-[(4-{2-[benzyl(hexyl)amino]-2-oxoethyl}phenoxy)methyl]benzoate (4-{[2-(Methoxycarbonyl)benzyl]oxy}phenyl)acetic acid (50 mg, 0.166 mmol) was dissolved in DCM (2 ml), N-hexylbenzylamine (38.2 mg, 0.2 mmol) was added, then EDC (38.3 mg, 0.2 mmol) was added and then DMAP (24.4 mg, 0.2 mmol) was added. The mixture was stirred at room temperature overnight. 1% HCl (1 ml) and water (1 ml) were added into the mixture. The two phases were separated by using a Whatman Filter Tube. The obtained organic solution was evaporated in vacuum and the oil product (71 mg) was left. It was then used directly in next step.

$^1$H NMR (rotamers, 500 MHz, CDCl$_3$): δ 0.86-0.91 (m, 3H), 1.22-1.32 (m, 6H), 1.47-1.58 (m, 2H), 3.21, 3.39 (t, t, 2H), 3.65, 3.75 (s, s, 2H), 3.93 (s, 3H), 4.53, 4.64 (s, s, 2H), 5.51, 5.52 (s, s, 2H), 6.96, 6.99 (d, d, 2H), 7.16 (d, 2H), 7.23-7.42 (m, 6H), 7.59 (t, 1H), 7.78 (d, 1H) and 8.06 (d, 1H).

c) 2-[(4-{2-[Benzyl(hexyl)amino]-2-oxoethyl}phenoxy)methyl]benzoic acid

Methyl 2-[(4-{2-[benzyl(hexyl)amino]-2-oxoethyl}phenoxy)methyl]benzoate (70 mg, 0.148 mmol) in THF (2 ml) was cooled in an ice-bath. Lithium hydroxide (7.08 mg, 0.296 mmol) in water (1 ml) was dropped in. The cooling-bath was then removed and the mixture was stirred overnight. HPLC showed that the reaction was not complete. More lithium hydroxide (0.2M, 0.5 ml) was added. The reaction mixture was stirred for 4 days more. It was then evaporated in vacuum to remove THF. The residue was acidified with 1% hydrochloric acid, pH=3-4, and extracted with ethyl acetate. The organic phase was dried (magnesium sulphate) and evaporated. Chromatography of the residue on a column (ISOLUTE® SI, 2 g/6 ml) using DCM, MeOH/DCM (1:99, and then 2:98) as eluant gave 24 mg the desired product, yield 35%.

$^1$H NMR (rotamers, 500 MHz, CDCl$_3$): δ 0.86-0.90 (m, 3H), 1.21-1.30 (m, 6H), 1.46-1.58(m, 2H), 3.21, 3.39 (t, t, 2H), 3.68, 3.77 (s, s, 2H), 4.53, 4.65 (s, s, 2H), 5.53, 5.54 (s, s, 2H), 6.95, 6.98 (d, d, 2H), 7.14-7.17 (m, 2H), 7.22-7.33 (m, 4H), 7.35-7.43 (m, 2H), 7.60 (t, 1H), 7.80 (d, 1H) and 8.16 (d, 1H). $^{13}$C NMR (rotamers, 125 MHz, CDCl$_3$): δ 13.94, 13.97, 22.49, 22.53, 26.47, 26.57, 27.29, 28.36, 31.40, 31.50, 39.82, 40.12, 46.50, 47.43, 48.28, 51.31, 68.21, 115.15, 126.25, 126.85, 127.20, 127.24, 127.36, 127.48, 127.54, 127.97, 128.49, 128.87, 129.76, 129.89, 131.52, 133.18, 136.80, 137.57, 140.40, 157.59, 170.60, 171.76 and 172.03.

Example 4 a) Methyl 2-[(4-{2-[(2,4-difluorobenzyl)(heptyl)amino]-2-oxoethyl}phenoxy)methyl]-benzoate N-(2,4-Difluorobenzyl)-N-heptylamine (106 mg, 0.44 mmol) was added into (4-{[2-(methoxycarbonyl)benzyl]oxy}phenyl)acetic acid (120 mg, 0.4 mmol) in DCM (10 ml) and followed by EDC (84.3 mg, 0.44 mmol) and then DMAP (54 mg, 0.44 mmol). The mixture was stirred at room temperature overnight, and then washed with 1% hydrochloric acid, water and brine and dried with magnesium sulphate and evaporated. Chromatography of the residue on a column (ISOLUTE®SI, 5 g/15 ml) using DCM and MeOH/DCM (0.5:99.5) as eluant gave 155 mg desired product, yield 74%.

$^1$H NMR (rotamers, 500 MHz, CDCl$_3$): δ 0.88-0.92 (m, 3H), 1.23-1.33 (m, 8H), 1.49-1.57 (m, 2H), 3.24, 3.34 (t, t, 2H), 3.66, 3.72 (s, s, 2H), 3.92 (s, 3H), 4.53, 4.62 (s, s, 2H), 5.50, 5.51 (s, s, 2H), 6.77-6.89 (m, 2H), 6.95, 6.98 (d, d, 2H), 6.99-7.04, 7.29-7.33 (m, m, 1H), 7.17, 7.20 (d, d, 2H), 7.39 (t, 1H), 7.57 (t, 1H), 7.75-7.79 (m, 1H) and 8.05 (d, 1H).

b) 2-[(4-{2-[(2,4-Difluorobenzyl)(heptyl)amino]-2-oxoethyl}phenoxy)methyl]benzoic acid Lithium hydroxide (13.3 mg, 0.554 mmol) in water (1.5 ml) was added into 70335 methyl 2-[(4-{2-[(2,4-difluorobenzyl)(heptyl)amino]-2-oxoethyl}phenoxy)methyl]benzoate (145 mg, 0.277 mmol) dissolved in THF (3 ml). The mixture was then in microwave oven (Smith Synthesizer) at 150° C. for 7 minutes and then evaporated to remove THF. The residue was acidified with 1% hydrochloric acid, pH~4 and then extracted with ethyl acetate (×2). The organic portions were combined, washed with brine, dried with magnesium sulphate and then evaporated. Chromatography of the residue on a column (ISOLUTE® SI, 2 g/6 ml) using DCM then MeOH/DCM (0.5:99.5, then 1:99) as eluant gave 94 mg desired product, yield 67%.

$^1$H NMR (rotamers, 500 MHz, CDCl$_3$): δ 0.86-0.91 (m, 3H), 1.22-1.32 (m, 8H), 1.48-1.56 (m, 2H), 3.23, 3.34 (t, t, 2H), 3.68, 3.73 (s, s, 2H), 4.52, 4.63 (s, s, 2H), 5.53 (s, br, 2H), 6.77-6.87 (m, 2H), 6.93-6.97 (m, 2H), 6.99-7.04, 7.27-7.33 (m, m, 1H), 7.16-7.20 (m, 2H), 7.41 (t, 1H), 7.58-7.62 (m, 1H), 7.78 (d, 1H) and 8.15 (d, 1H). $^{13}$C NMR (rotamers, 125 MHz, CDCl$_3$): δ 14.00, 22.51, 26.75, 26.84, 27.26, 28.54, 28.86, 28.94, 31.64, 31.70, 39.75, 40.08, 41.39, 45.05, 46.30, 47.98, 68.21, 103.67 (t), 104.12 (t), 111.52 (d), 115.17, 119.80 (d), 120.52 (d), 126.97, 127.04, 127.21, 128.81 (br), 129.78, 129.85, 131.52, 133.16, 140.33, 157.65, 160.48 (dd), 160.85 (dd), 162.13 (dd), 162.46 (dd), 171.01, 171.93 and 171.99.

Example 5 a) N-(2,4-difluorobenzyl)-N-heptyl-3-(4-hydroxyphenyl)propanamide 3-(4-Hydroxyphenyl)propionic acid (108 mg, 0.650 mmol) was dissolved in DMF. N-(2,4-difluorobenzyl)-N-heptylamine (164.7 mg, 0.682 mmol) was added. The mixture was cooled in an ice-bath. TBTU (219 mg, 0.682 mmol) was added and followed by DIPEA (0.238 ml, 1.365 mmol). The mixture was stirred overnight and the temperature was allowed up to room temperature. Ethyl acetate and sodium hydrogencarbonate aqueous solution (sat.) were added and then the two phases were separated. The water phase was extracted with ethyl acetate. The organic phases were combined and dried with magnesium sulphate and evaporated. Chromatography of the residue on a column (ISOLUTE® SI, 5 g/15 ml) using DCM and then MeOH/DCM (1:99) as eluant gave 223 mg desired product, yield 88%.

$^1$H NMR (rotamers, 500 MHz, CDCl$_3$): δ 0.86-0.90 (m, 3H), 1.21-1.31 (m, 8H), 1.47-1.53 (m, 2H), 2.60, 2.67 (t, t, 2H), 2.85-2.96 (m, 2H), 3.15, 3.32 (t, t, 21), 4.41, 4.60 (s, s, 2H), 6.75-6.85 (m, 4H), 6.90-6.96, 7.12-7.18 (m, m, 1H) and 7.00, 7.04 (d, d, 2H).

b) Methyl 2-[(4-{3-[(2,4-difluorobenzyl)(heptyl)amino]-3-oxopropyl}phenoxy)methyl]-benzoate N-(2,4-difluorobenzyl)-N-heptyl-3-(4-hydroxyphenyl)propanamide (195 mg, 0.501 mmol), 2-bromomethylbenzoic acid methyl ester (120.4 mg, 0.526 mmol) and anhydrous potassium carbonate (103 mg, 0.751 mmol) were mixed in acetonitrile (15 ml). The mixture was heated to reflux overnight and then evaporated to dryness. Water and ethyl acetate were added and the two phases were separated. The organic phase was dried (magnesium sulphate) and evaporated. Chromatography of the residue on a column (ISOLUTE® SI, 2 g/6 ml) using heptane/DCM (50:50), then DCM and then MeOH/DCM (0.5:99.5) as eluant gave 187 mg desired product, yield 69.5%.

$^1$H NMR (rotamers, 500 MHz, CDCl$_3$): δ 0.87-0.91 (m, 3H), 1.21-1.31 (m, 8H), 1.44-1.56 (m, 2H), 2.56-2.69 (m, 2H), 2.91-3.01 (m, 2H), 3.14, 3.32 (t, t, 2H), 3.92 (s, 3H), 4.43, 4.59 (s, s, 2H), 5.49 (s, 2H), 6.75-6.97 (m, 4H), 7.08-7.28 (m, 3H), 7.38 (t, 1H), 7.56 (t, 1H), 7.76 (d, 1H) and 8.04 (d, 1H), c) 2-[(4-{3-[(2,4-Difluorobenzyl)(heptyl)amino]-3-oxopropyl}phenoxy)methyl]benzoic acid Lithium hydroxide (13.3 mg, 0.554 mmol) in water (1 ml) was added into methyl 2-[(4-{3-[(2,4-difluorobenzyl)(heptyl)amino]-3-oxopropyl}phenoxy)methyl]benzoate (149 mg, 0.277 mmol) dissolved in THF (2 ml). The mixture was then placed in microwave oven (Smith Synthesizer) at 150° C. for 7 minutes and then evaporated to remove THF. The residue was acidified with 1% hydrochloric acid, pH~4, and extracted with ethyl acetate (×2). The organic extracts were combined and washed with brine and dried with magnesium sulphate and then evaporated. Chromatography of the residue on a column (ISOLUTE® SI, 2 g/6 ml) using DCM, then MeOH/DCM (1:99) as eluant gave 121 mg desired product, yield 83%.

$^1$H NMR (rotamers, 500 MHz, CDCl$_3$): δ 0.89-0.93 (m, 3H), 1.24-1.33 (m, 8H), 1.49-1.58 (m, 2H), 2.64-2.74 (m, 2H), 2.97-3.03 (m, 2H), 3.17, 3.37 (t, t, 2H), 4.46, 4.65 (s, s, 2H), 5.58, 5.59 (s, s, 2H), 6.78-6.87 (m, 2H), 6.94-6.97 (m, 2H), 6.99-7.04, 7.27-7.31 (m, m, 1H), 7.14, 7.17 (d, d, 2H), 7.42-7.45 (m, 1H), 7.61-7.64 (m, 1H), 7.82-7.85 (m, 1H) and 8.19-8.22 (d, 1H), $^{13}$C NMR (rotamers, 125 MHz, CDCl$_3$): δ 13.96, 22.46, 22.49, 26.67, 26.85, 27.38, 28.57, 28.80, 28.94, 30.69, 30.84, 31.58, 31.67, 35.01, 35.26, 41.63, 44.76, 44.78, 46.43, 47.78, 68.15, 103.60(t), 104.07(t), 111.41(dd), 111.49 (dd), 114.91, 119.74 (d), 120.45 (d), 126.86, 127.12, 128.53 (br), 129.40, 131.49, 131.58, 133.15, 133.32, 140.54, 157.12, 160.33 (dd), 160.81 (dd), 162.07 (dd), 162.33 (dd), 171.07, 173.04 and 173.11.

Example 6 a) 3-(4-Mercaptophenyl)propanoic acid (2.0 g, 10.97 mmol) was dissolved in dry THF (60 ml) and cooled to 0° C. Sodium hydride (0.64 g, 24.1 mmol) was added. The mixture was stirred for 30 minutes, methyl 2-(bromomethyl)benzoate (2.77 g, 12.07 mmol) dissolved in dry THF (10 ml) was added dropwise. The solution was allowed to warm up to room temperature and was stirred overnight. Dropwise addition of water (10 ml) deactivated the remaining sodium hydride. The solvent was removed by evaporation, and the residue was acidified to pH 3 (HCl 1%). The water phase was washed with EtOAc (3×10 ml). The organic phases was combined, dried (MgSO$_4$) and evaporated. The crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two potions of brine and dried (MgSO$_4$). Removing the solvent by evaporation gave 2.26 gram of 3-(4-{[2-(methoxycarbonyl)benzyl]thio}phenyl)propanoic acid (yield 62.3%).

$^1$H NMR (500 MHz, CDCl$_3$): δ 2.66 (t, 2H), 2.92 (t, 2H), 3.90 (s, 3H), 4.51 (s, 2H), 7.10 (d, 2H), 7.19 (d, 1H), 7.25 (d, 2H), 7.29 (t, 1H), 7.36 (t, 1H) and 7.94 (d, 1H).

b) Methyl 2-{[(4-{3-[(2,4-difluorobenzyl)(heptyl)amino]-3-oxopropyl}phenyl)thio]methyl}benzoate N-(2,4-difluorobenzyl)-N-heptylamine (0.64 g, 2.65 mmol) was dissolved in DMF (10 ml), 3-(4-{[2-(methoxycarbonyl)benzyl]thio}phenyl)propanoic acid (0.80 g, 2.41 mmol) was added and the mixture was cooled to 0° C. N-[(1H-1,2,3-benzotriazol-1-yloxy)-(dimethylamino)methylene]-N-methylmethanaminium tetrafluoroborate (0.85 g, 2.65 mmol) and diisopropylethylamine (0.65 g, 5.05 mmol) was added. The mixture was allowed to warm to room temperature and stirred overnight. EtOAc (15 ml) was added and the organic phase was washed with two portions of sodium hydrogencarbonate (aq, 10 ml). EtOAc was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation and gave 1.10 gram of methyl 2-{[(4-{3-[(2,4-difluorobenzyl)(heptyl)amino]-3-oxopropyl}phenyl)thio]methyl}benzoate (yield 82.2%).

$^1$H NMR (rotamers, 500 MHz, CDCl$_3$): δ 0.89 (t, 3H), 1.22-1.32 (m, 8H), 1.47-1.55 (m, 2H), 2.55, 2.66 (t, t, 2H), 2.95-3.01 (m, 2H), 3.16, 3.33 (t, t, 2H), 3.89, 3.90 (s, s, 3H), 4.44, 4.60 (s, s, 2H), 4.50, 4.51 (s, s, 2H), 6.76-6.85 (m, 2H), 6.92-6.96, 7.20-7.25 (m, m, 4H), 7.07, 7.12 (d, d, 2H), 7.27-7.31 (m, 1H), 7.32-7.34 (m, 1H) and 7.91-7.92 (m, 1H).

c) 2-{[(4-{3-[(2,4-Difluorobenzyl)(heptyl)amino]-3-oxopropyl}phenyl)thio]methyl}benzoic acid Methyl 2-{[(4-{3-[(2,4-difluorobenzyl)(heptyl)amino]-3-oxopropyl}phenyl)thio]methyl}benzoate (1.05 g, 1.89 mmol) was dissolved in EtOH (95%, 5 ml), potassium hydroxide (0.21 g, 3.77 mmol) was added. The reaction was performed in a single node microwave oven (7 min, 150° C.). Workup was by addition of EtOAc (5 ml) and washing with HCl (2×5 ml, 1M). The organic layer was dried (MgSO$_4$) and the solvent was removed by evaporation to give 0.96 gram of 2-{[(4-{3-[(2,4-difluorobenzyl)(heptyl)amino]-3-oxopropyl}phenyl)thio]methyl}benzoic acid (yield 94.3%).

$^1$H NMR (rotamers, 500 MHz, CDCl$_3$): δ 0.88-0.92 (m, 3H), 1.24-1.33 (m, 8H), 1.50-1.57 (m, 2H), 2.64, 2.69 (t, t, 2H), 2.95-3.00 (m, 2H), 3.20, 3.34 (t, t, 2H), 4.48, 4.62 (s, s, 2H), 4.55, 4.56 (s, s, 2H), 6.79-6.87 (m, 2H), 6.98-7.03, 7.27-7.30 (m, m, 2H), 7.06-7.10 (m, 2H), 7.22-7.24 (m, 2H), 7.31-7.36 (m, 1H), 7.41-7.46 (m, 1H) and 8.03 (d, 1H). $^{13}$C NMR (rotamers, 125 MHz, CDCl$_3$): δ 14.01, 22.51, 22.54, 26.74, 26.90, 27.42, 28.63, 28.86, 28.98, 30.92, 31.18, 31.64, 31.72, 34.65, 38.23, 38.28, 41.58, 44.82, 46.44, 47.77, 103.46 (t), 104.14(t), 111.52(dd), 111.58(dd), 119.74 (dd), 120.51(dd), 127.09, 128.55, 128.63, 129.03, 131.16, 131.49, 131.55, 131.78 (dd), 132.30, 132.50, 132.96, 140.04, 140.11, 140.59, 140.68, 160.47(dd), 160.88(dd), 162.16(dd), 162.44(dd), 170.88(br), 172.56 and 172.59.

Example 7 a) N-(2,3-dimethoxybenzyl)butan-1-amine (0.59 g, 2.65 mmol) was dissolved in DMF (10 ml), 3-(4-hydroxyphenyl)propanoic acid (0.4 g, 2.41 mmol), was added and the mixture was cooled to 0° C. N-[(1H-1,2,3-benzotriazol-1-yloxy)(dimethylamino)methylene]-N-methylmethanaminium tetrafluoroborate (0.85 g, 2.65 mmol) and diisopropylethylamine (0.65 g, 5.05 mmol) was added. The mixture was allowed to warm to room temperature and stirred over night. EtOAc (15 ml) was added and the organic phase was washed with two portions of sodium hydrogencarbonate (aq, 10 ml). EtOAc was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two potions of brine and dried (MgSO$_4$). The solvent was removed by evaporation and gave 1.08 gram of N-butyl-N-(2,3-dimethoxybenzyl)-3-(4-hydroxyphenyl)propanamide (yield 82.3%).

$^1$H NMR (rotamers, 500 MHz, CDCl$_3$): δ 0.85-0.89 (m, 3H), 1.20-1.30 (m, 2H), 1.44-1.53 (m, 2H), 2.60, 2.65 (t, t, 2H), 2.88, 2.94 (t, t, 2H), 3.13, 3.33 (t, t, 2H), 3.78, 3.80 3.83, 3.85 (s, s, s, s, 6H), 4.43, 4.68 (s, s, 2H), 6.57, 6.67 (d, d, 1H), 6.74-6.86 (m, 3H) and 6.95-7.05 (m, 3H).

b) N-butyl-N-(2,3-dimethoxybenzyl)-3-(4-hydroxyphenyl)propanamide (50 mg, 0.13 mmol) and methyl 2-(bromomethyl)benzoate (0.034 g, 0.15 mmol) was dissolved in acetonitrile (10 ml) and potassium carbonate (37 mg, 0.27 mmol) was added. The mixture was stirred at 60° C. for three hours. Polymer supported trisamine (0.3 eqv) was added and stirred overnight. The polymer was filtered off and solvent was removed by evaporation. EtOAc (10 ml) was added and the organic phase was washed with three portions of water. After drying the crude (MgSO$_4$), the solvent had been removed by evaporation. The residue was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). Removing the solvent by evaporation gave 15 mg of methyl 2-[(4-{3-[butyl(2,3-dimethoxybenzyl)amino]-3-oxopropyl}phenoxy)methyl]benzoate (21.4%).

$^1$H NMR (rotamers, 500 MHz, CDCl$_3$): δ 0.89-0.95 (m, 3H), 1.24-1.35 (m, 2H), 1.48-1.57 (m, 2H), 2.62, 2.69 (t, t, 2H), 2.95, 3.01 (t, t, 2H), 3.17, 3.36 (t, t, 2H), 3.83, 3.86, 3.89, 3.90, 3.93, 3.94 (s, s, s, s, s, s, 9H), 4.48, 4.71 (s, s, 2H), 5.50, 5.52 (s, s, 2H), 6.62, 6.75 (d, d, 1H), 6.84-6.97 (m, 3H), 7.00-7.04 (m, 1H), 7.11, 7.19 (d, d, 2H), 7.38-7.42 (m, 1H), 7.56-7.60 (m, 1H), 7.78 (t, 1H) and 8.04-8.07 (m, 1H).

c) Methyl 2-[(4-{3-[butyl(2,3-dimethoxybenzyl)amino]-3-oxopropyl}phenoxy)methyl]-benzoate (15 mg, 0.029 mmol) was dissolved in THF/water (2/1, 2 ml) and LiOH (1.4 mg, 0.058 mmol) was added. The reaction was performed in a single node microwave oven (150° C., 7 min). Workup was done by adding EtOAc (10 ml) and washing the organic phase with two portions of HCl (2×5 ml, 1 M). The organic phase was dried (MgSO$_4$) and the solvent was removed by evaporation to give 13 mg of 2-[(4-{3-[butyl (2,3-dimethoxybenzyl)amino]-3-oxopropyl}phenoxy)methyl]benzoic acid (yield 89%).

$^1$H NMR (rotamers, 500 MHz, CDCl$_3$): δ 0.89-0.95 (m, 3H), 1.24-1.35 (m, 2H), 1.48-1.57 (m, 2H), 2.62, 2.69 (t, t, 2H), 2.95, 3.01 (t, t, 2H), 3.17, 3.36 (t, t, 2H), 3.83, 3.85, 3.88, 3.89 (s, s, s, s, 6H), 4.48, 4.71 (s, s, 2H), 5.50, 5.52 (s, s, 2H), 6.62, 6.75 (d, d, 1H), 6.84-6.97 (m, 3H), 7.00-7.04 (m, 1H), 7.11, 7.19 (d, d, 2H), 7.38-7.42 (m, 1H), 7.56-7.60 (m, 1H), 7.78 (t, 1H) and 8.04-8.07 (m, 1H). $^{13}$C NMR (rotamers, 125 MHz, CDCl$_3$): δ 13.76, 13.85, 20.02, 20.21, 29.55, 30.30, 30.69, 30.84, 30.96, 35.13, 35.34, 42.60, 46.17, 46.37, 47.20, 55.69, 55.75, 60.35, 61.74, 68.20, 111.23, 111.79, 114.88, 114.96, 118.79, 120.88, 124.15, 124.21, 126.81, 127.18, 127.26, 129.46, 130.51, 131.25, 131.52, 133.23, 133.65, 140.59, 146.50, 147.17, 152.48, 152.61, 157.02, 157.10, 170.79, 172.93 and 173.25.

Example 8 a) N-(2,3-Dimethoxybenzyl)-N-heptylamine (0.70 g, 2.65 mmol) was dissolved in DM (10 ml), 3-(4-hydroxyphenyl) propanoic acid (0.4 g, 2.41 mmol), was added and the mixture was cooled to 0° C. N-[(1H-1,2,3-benzotriazol-1-yloxy)(dimethylamino)methylene]-N-methylmethanaminium tetrafluoroborate (0.85 g, 2.65 mmol) and diisopropylethylamine (0.65 g, 5.05 mmol) was added. The mixture was allowed to warm to room temperature and stirred overnight. EtOAc (15 ml) was added and the organic phase was washed with two portions of sodium hydrogencarbonate (aq, 10 ml). EtOAc was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation and gave 0.98 gram N-(2,3-dimethoxybenzyl)-N-heptyl-3-(4-hydroxyphenyl)propanamide (yield 70%).

$^1$H NMR (rotamers, 500 MHz, CDCl$_3$): δ 0.85-0.89 (m, 3H), 1.20-1.30 (m, 8H), 1.47-1.56 (m, 2H), 2.62, 2.67 (t, t, 2H), 2.89, 2.95 (t, t, 2H), 3.14, 3.33 (t, t, 2H), 3.79, 3.80, 3.84, 3.85 (s, s, s, s, 6H), 4.45, 4.69 (s, s, 2M), 6.58, 6.68 (d, d, 1H), 6.74-6.88 (m, 3H) and 6.96-7.05 (m, 3H).

b) N-(2,3-dimethoxybenzyl)-N-heptyl-3-(4-hydroxyphenyl)propanamide 0.196 g, 0.47 mmol) and methyl 2-(bromomethyl)benzoate (0.12 g, 0.52 mmol) was dissolved in acetonitrile (10 ml) and potassiumcarbonate (131 mg, 0.95 mmol) was added. The mixture was stirred at 60° C. for three hours. Polymersuproted trisamine (0.3 eqv) was added and stirred over night. The polymer was filtered of, solvent was removed by evaporation, addition of EtOAc (10 ml) and the organic phase was washed with three potions of water. After drying the crude (MgSO$_4$) and the solvent had been removed by evaporation, the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two potions of brine and dried (MgSO$_4$). Removing the solvent by evaporation gave 39 mg of methyl 2-[(4-{3-[(2,3-dimethoxybenzyl)(heptyl)amino]-3-oxopropyl}phenoxy)methyl]benzoate (yield 14.6%).

$^1$H NMR (rotamers, 500 MHz, CDCl$_3$): δ 0.86-0.89 (m, 3H), 1.19-1.30 (m, 8H); 1.46-1.55 (m, 2H), 2.60, 2.66 (t, t, 2H), 2.93, 2.98 (t, t, 2H), 3.14, 3.33 (t, t, 2H), 3.80, 3.83, 3.86, 3.87, 3.90, 3.91 (s, s, s, s, s, s, 9H), 4.45, 4.68 (s, s, 2H), 5.48, 5.49 (s, s, 2H), 6.59, 6.73 (d, d, 1H), 6.81-7.01 (m, 4H) 7.08, 7.16 (d, d, 2H) 7.35-7.39 (m, 1H), 7.53-7.57 (m, 1H), 7.76 (t, 1H) and 8.01-8.04 (m, 1H).

c) Methyl 2-[(4-{3-[(2,3-dimethoxybenzyl)(heptyl) amino]-3-oxopropyl}phenoxy)methyl]-benzoate (39 mg, 0.069 mmol) was dissolved in THF/water (2/1, 2 ml) and LiOH (3.3 mg, 0.14 mmol) was added. The reaction was performed I a single node microwave oven (150° C., 7 min). Workup was done by adding EtOAc (10 ml) and washing the organic phase with two potions of HCl (2×5 ml, 1 M). The organic phase was dried (MgSO$_4$) and the solvent was removed by evaporation to give 30 mg of 2-[(4-{3-[(2,3-dimethoxybenzyl)(heptyl)-amino]-3-oxopropyl}phenoxy) methyl]benzoic acid (yield 78.9).

$^1$H NMR (rotamers, 500 MHz, CDCl$_3$): δ 0.84-0.87 (m, 3H), 1.20-1.28 (m, 8H), 1.45-1.55 (m, 2H), 2.63, 2.69 (t, t, 2H), 2.93, 2.99 (t, t, 2H), 3.13, 3.33 (t, t, 2H), 3.79, 3.81, 3.84, 3.85 (s, s, s, s, 6H), 4.45, 4.69 (s, s, 2H), 5.52, 5.53 (s, s, 2H), 6.60, 6.72 (d, d, 1H), 6.79-7.01 (m, 4H) 7.08, 7.16 (d, d, 2H) 7.36-7.41 (m, 1H), 7.55-7.60 (m, 1H), 7.79 (t, 1H) and 8.13-8.16 (m, 1H). $^{13}$C NMR (rotamers, 125 MHz, CDCl$_3$): δ 14.04, 22.52, 22.56, 26.77, 26.96, 27.45, 28.60, 28.92, 29.03, 30.83, 30.97, 31.66, 31.75, 35.16, 35.36, 42.61, 46.42, 46.46, 47.45, 55.69, 55.75, 60.35, 60.73, 68.19, 111.26, 111.83, 114.88, 114.95, 118.84, 120.91, 124.14, 124.20, 126.85, 127.15, 127.22, 129.46, 130.52, 131.26, 131.51, 133.19, 133.66, 140.61, 146.59, 147.19, 152.48, 152.60, 157.02, 157.11, 170.77, 172.92 and 173.23.

Example 9 a) N-(3-ethoxypropyl)-N-(4-isopropylbenzyl)amine p-iso-Propylbenzaldehyde (1.007 g, 6.798 mmol) was dissolved in methanol (5 ml). Trimethyl orthoformate (5 ml) was added. 3-Ethoxypropylamine (681 mg, 6.6 mmol) was then added and followed by acetic acid (0.2 ml). After standing at room temperature overnight, DCM (5 ml) was added and followed by borohydride on polymer support (5.28 g, 13.2 mmol). The mixture was shaken at room temperature for 4 days and then filtered. The filtrate was evaporated. The residue was dissolved in acetonitrile, then divided into two portions and loaded on 2 columns (ISO-LUTE® PRS, 10 g/70 ml, wetted with acetonitrile). It was eluted with acetonitrile, then methanol and then methanol (NH$_3$ sat.). The product fractions were combined and evaporated. Oil product 1.283 g was obtained, yield 83%.

$^1$H NMR (300 MHz, CDCl$_3$): δ 1.19 (t, 3H), 1.25 (d, 6H), 1.75-1.84 (m, 2H), 2.73 (t, 2H), 2.85-2.94 (m, 1H), 3.43-3.52 (m, 4H), 3.75 (s, 2H), 7.18 (d, 2H) and 7.24 (d, 2H).

b) N-(3-ethoxypropyl)-N-(4-isopropylbenzyl)amine (0.62 g, 2.65 mmol) was dissolved in DMF (10 ml), 3-(4-hydroxyphenyl)propanoic acid (0.4 g, 2.41 mmol), was added and the mixture was cooled to 0° C. N-[(1H-1,2,3-benzotriazol-1-yloxy)(dimethylamino)-methylene]-N-methylmethanaminium tetrafluoroborate (0.85 g, 2.65 mmol) and diisopropylethylamine (0.65 g, 5.05 mmol) was added. The mixture was allowed to warm to room temperature and stirred overnight. EtOAc (15 ml) was added and the organic phase was washed with two portions of sodium hydrogencarbonate (aq, 10 ml). EtOAc was removed by evaporation and the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation and gave 1.0 gram of N-(3-ethoxypropyl)-3-(4-hydroxyphenyl)-N-(4-isopropylbenzyl)propanamide (yield 75.8%).

$^1$H NMR (rotamers, 500 MHz, CDCl$_3$): δ 1.16-1.21 (m, 3H), 1.26, 1.27 (d, d, 6H), 1.75-1.80, 1.84-1.90 (m, m, 2H), 2.64, 2.74 (t, t, 2H), 2.86-3.00 (m, 3H), 3.33, 3.37 (t, t, 2H), 3.41-3.50 (m, 4H), 4.43, 4.62 (s, s, 2H), 6.80-6.84 (m, 2H) and 6.97-7.22 (m, 6H).

c) N-(3-ethoxypropyl)-3-(4-hydroxyphenyl)-N-(4-isopropylbenzyl)propanamide (0.18 g, 0.47 mmol) and methyl 2-(bromomethyl)benzoate (0.12 g, 0.52 mmol) was dissolved in acetonitrile (10 ml) and potassium carbonate (131 mg, 0.95 mmol) was added. The mixture was stirred at 60° C. for three hours. Polymer-supported trisamine (0.3 eqv) was added and stirred overnight. The polymer was filtered off, solvent was removed by evaporation, addition of EtOAc (10 ml) and the organic phase was washed with three portions of water. After drying the crude (MgSO$_4$) and the solvent had been removed by evaporation, the crude was purified by preparative HPLC (started with acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two potions of brine and dried (MgSO$_4$). Removing the solvent by evaporation gave 0.16 gram of methyl 2-[(4-{3-[(3-ethoxypropyl)(4-isopropylbenzyl)amino]-3-oxopropyl}phenoxy)methyl]benzoate (yield 63.5%).

$^1$H NMR (rotamers, 500 MHz, CDCl$_3$): δ 1.17, 1.21 (t, t, 3H), 1.27, 1.28 (d, d, 6H), 1.75-1.80, 1.84-1.89 (m, m, 2H), 2.63, 2.73 (t, t, 2H), 2.89-3.04 (m, 3H), 3.32, 3.37 (t, t, 2H), 3.41-3.50 (m, 4H), 3.93, 3.94 (s, s, 3H), 4.46, 4.61 (s, s, 2H), 5.51, 5.53 (s, s, 2H), 6.92, 6.95 (d, d, 2H), 7.04-7.22 (m, 6H), 7.40 (t, 1H), 7.58 (t, 1H), 7.78-7.80 (m, 1H) and 8.05-8.07 (m, 1H).

d) Methyl 2-[(4-{3-[(3-ethoxypropyl)(4-isopropylbenzyl) amino]-3-oxopropyl}phenoxy)methyl]benzoate (0.16 g, 0.30 mmol) was dissolved in THF/water (2/1, 2 ml) and LiOH (14.4 mg, 0.60 mmol) was added. The reaction was performed in a single node microwave oven (150° C., 7 min). Workup was done by adding EtOAc (10 ml) and washing the organic phase with two portions of HCl (2×5 ml, 1 M). The organic phase was dried (MgSO$_4$) and the solvent was removed by evaporation to give 0.108 gram of 2-[(4-{3-[(3-ethoxypropyl)(4-isopropylbenzyl)amino]-3-oxopropyl}phenoxy)methyl]benzoic acid (yield 69.3%).

$^1$H NMR (rotamers, 500 MHz, CDCl$_3$): δ 1.15, 1.19 (t, t, 3H), 1.23-1.25 (m, 6H), 1.74-1.79, 1.84-1.89 (m, m, 2H), 2.66, 2.76 (t, t, 2H), 2.86-3.03 (m, 3H), 3.30, 3.36 (t, t, 2H), 3.40-3.50 (m, 4H), 4.44, 4.61 (s, s, 2H), 5.55, 5.56 (s, s, 2H), 6.90-6.94 (m, 2H), 7.02-7.20 (m, 6H), 7.40 (t, 1H), 7.57-7.60 (m, 1H), 7.79-7.82 (m, 1H) and 8.15-8.18 (m, 1H). $^{13}$C NMR (rotamers, 125 MHz, CDCl$_3$): δ 15.15, 23.98, 27.78, 28.61, 30.93, 31.01, 33.73, 35.07, 35.38, 43.86, 44.13, 47.96, 51.26, 66.06, 66.22, 66.82, 67.98, 68.13, 114.77, 126.03, 126.38, 126.72, 126.97, 127.90, 129.31, 131.31, 132.88, 133.23, 133.39, 133.84, 134.56, 140.30, 140.38, 147.71, 148.05, 156.90, 170.48, 173.02 and 173.26.

Example 10 a) N-(2,4-difluorobenzyl)-N-propylamine 2,4-Difluorbenzaldehyde (1.003 g, 7.055 mmol) was dissolved in methanol (5 ml). Trimethyl orthoformate (5 ml) was added. Propylamine (401 mg, 6.784 mmol) was then added and followed by acetic acid (0.2 ml). After 1 hour, DCM (5 ml) was added and followed by borohydride polymer-supported (2.5 mmol/g, 5.42 g, 13.55 mmol). The mixture was shaken at room temperature for 4 days and then filtered. The filtrate was evaporated. The residue was dissolved in acetonitrile, then divided into two portions and loaded on two columns (ISOLUTE®PRS, 10 g/70 ml, wetted with acetonitrile). It was eluted with acetonitrile, then methanol and then methanol (NH$_3$ sat.). The product fractions were combined and evaporated. Oil product (892 mg) was obtained, yield 71%.

$^1$H NMR (400 MHz, CDCl$_3$): δ 0.91 (t, 3H), 1.47-1.56 (m, 2H), 2.57 (t, 2H), 3.79 (s, 2H), 6.75-6.85 (m, 2H) and 7.27-7.33 (m, 1H).

b) N-(2,4-difluorobenzyl)-3-(4-hydroxyphenyl)-N-propylpropanamide 3-(4-Hydroxyphenyl)propionic acid (245 mg, 1.474 mmol) in DMF (5 ml) was cooled in an ice-bath. N-(2,4-Difluorobenzyl)-N-propylamine (300.4 mg, 1.622 mmol) was added and then TBTU (521 mg, 1.622 mmol) followed by DIPEA (400 mg, 3.096 mmol). The mixture was stirred at room temperature overnight. Sodium hydrogencarbonate aqueous solution (sat.) was added. The mixture was extracted with ethyl acetate (×2). The extracts were combined and dried (magnesium sulphate) and evaporated. Chromatography of the residue on a column (ISOLUTE® SI, 5 g/25 ml) using DCM/heptane (50:50), DCM and then MeOH/DCM (1:99, then 2:98) as eluant gave 336 mg the desired product, yield 68%.

$^1$H NMR (rotamers, 300 MHz, CDCl$_3$): δ 0.82-0.88 (m, 3H), 1.45-1.58 (m, 2H), 2.59, 2.65 (t, t, 2H), 2.88-2.98 (m, 2H), 3.11, 3.27 (t, t, 2H), 4.40, 4.59 (s, s, 2H), 6.71-7.03 (m, 6H), 7.07-7.16 (m, 1H) and 7.79 (s, br, 1H).

c) Methyl 2-[(4-{3-[(2,4-difluorobenzyl)(propyl) amino]-3-oxopropyl}phenoxy)methyl]benzoate N-(2,4-Difluorobenzyl)-3-(4-hydroxyphenyl)-N-propylpropanamide (290 mg, 0.87 mmol) was dissolved in acetonitrile (10 ml). 2-Bromomethyl-benzoic acid methyl ester (209 mg, 0.913 mmol) was added followed by potassium carbonate, anhydrous (180 mg, 1.305 mmol). The mixture was heated to reflux overnight and then evaporated to dry. Water and ethyl acetate were added and two phases were separated. The organic phase was dried (magnesium sulphate) and evaporated. Chromatography of the residue on a column (ISOLUTE®SI, 20 g/70 ml) using DCM and then MeOH/DCM (1:99) as eluant gave 184 mg the desired product, yield 44%.

$^1$H NMR (rotamers, 500 MHz, CDCl$_3$): δ 0.85-0.92 (m, 3H), 1.52-1.60 (m, 2H), 2.61, 2.68 (t, t, 2H), 2.95-3.01 (m, 2H), 3.15, 3.32 (t, t, 2H), 3.92, 3.93 (s, s, 3H), 4.45, 4.62 (s, s, 2H), 5.51, 5.52 (s, s, 2H), 6.77-6.86 (m, 2H), 6.92-6.99, 7.23-7.27 (m, m, 3H), 7.12, 7.16 (d, d, 2H), 7.38-7.42 (m, 1H), 7.57 (t, 1H) 7.78 (d, 1H) and 8.04-8.07 (m, 1H).

d) 2-[(4-{3-[(2,4-difluorobenzyl)(propyl)amino]-3-oxopropyl}phenoxy)methyl]benzoic acid A mixture of methyl 2-[(4-{3-[(2,4-difluorobenzyl)(propyl)amino]-3-oxopropyl}phenoxy)methyl]benzoate (0.184 g, 0.382 mmol) and lithium hydroxide (0.018 g, 0.76 mmol) in THF (2 ml) and water (2 ml) was heated at 150 degrees for 7 minutes. The mixture was diluted with water, acidified with hydrochloric acid and extracted with methylene chloride. The combined extracts were dried with magnesium sulfate and evaporated to give 2-[(4-{3-[(2,4-difluorobenzyl)(propyl)amino]-3-oxopropyl}phenoxy)methyl]benzoic acid.

$^1$HNMR (400 MHz, CDCl$_3$): δ 0.85 (t, 3), 1.4-1.6 (m, 2), 2.6-2.7 (m, 2), 2.9-3.0 (m, 2), 3.05-3.15 and 3.25-3.35 (multiplets, rotamers, 2), 4.4 and 4.6 (singlets, rotamers, 2), 5.5 (m, 2), 6.7-6.8 (m, 2), 6.9-7.0 (m, 2), 7.05-7.2 (m, 2), 7.4 (t, 1), 7.6 (t, 1), 7.8 (d, 1), 8.15 (d, 1).

Example 11 a) Methyl 2-({[4-(2-{ethyl[4-(trifluoromethyl)benzyl]amino}-2-oxoethyl)phenyl]thio}methyl)benzoate Ethyl[4-(trifluoromethyl)benzyl]amine (284 mg, 1.40 mmol) and (4-{[2-(methoxycarbonyl)benzyl]thio}phenyl) acetic acid (443 mg, 1.40 mmol, See Example 2 b) were mixed in DMF (15 ml). TBTU (472 mg, 1.47 mmol) was added and then DIPEA (190 mg, 1.47 mmol) was added. The mixture was stirred at room temperature for 1 hour. EtOAc (20 ml) was added. The mixture was then washed with sodium hydrogencarbonate aqueous solution (sat.), 1% HCl, water (×2) and brine, dried with magnesium sulphate and evaporated. The title compound (663 mg) was left, yield 94%.

$^1$H NMR (rotamers, 500 MHz, CDCl$_3$): δ 1.08-1.15 (m, 3H), 3.31, 3.45 (q, q, 2H), 3.63, 3.76 (s, s, 2H), 3.92 (s, 3H), 4.52 4.66 (m, 4H), 7.09-7.40 (m, 8H), 7.56, 7.62 (d, d, 2H) and 7.94 (d, 2H).

b) 2-({[4-(2-{Ethyl[4-(trifluoromethyl)benzyl] amino}-2-oxoethyl)phenyl]thio}methyl)benzoic acid Methyl 2-({[4-(2-{ethyl[4-(trifluoromethyl)benzyl] amino}-2-oxoethyl)phenyl]thio}methyl)benzoate (640 mg, 1.276 mmol) was dissolved in THF (20 ml). Lithium hydroxide (61 mg, 2.552 mmol) in water (10 ml) was added. The mixture was stirred at room temperature and the reaction was followed by LC-MS. After 24 hours, more lithium hydroxide (30 mg) and water (10 ml) were added. After in total 70 hour, LC-MS showed the reaction was complete. The mixture was evaporated to remove THF. The residue was washed with diethyl ether, then acidified with 10% HCl, pH=2, and extracted with EtOAc (×2). The extracts were combined and washed with brine, dried with magnesium sulphate and evaporated. Chromatography of the residue on a column (ISOLUTE SI, 5 g/25 ml), using DCM and then MeOH/DCM (0.5:99.5, then 1:99) as eluant, gave the title compound (510 mg), yield 82%.

$^1$H NMR (rotamers, 300 MHz, CDCl$_3$): δ 1.07-1.15 (m, 3H), 3.31, 3.45 (q, q, 2H), 3.64, 3.77 (s, s, 2H), 4.54 (s, 2H), 4.55, 4.66 (s, s, 2H), 7.05-7.40 (m, 8H), 7.55, 7.60 (d, d, 2H) and 7.97 (d, 2H). $^{13}$C NMR (rotamers, 75 MHz, CDCl$_3$): δ 12.60, 13.80, 38.17, 38.25, 40.00, 40.44, 41.63, 42.40, 47.94, 50.61, 118-134 (complex multiplet), 140.32, 140.70, 141.50, 170.48 and 171.20.

Example 12

2-[(4-{2-[Ethyl(2-fluorobenzyl)amino]-2-oxoethyl}phenoxy)methyl]benzoic acid a) N-(2-Fluorobenzyl)ethanamine (0.554 g, 3.615 mmol) was dissolved in DMF (10 ml). (4-Hydroxyphenyl)acetic acid (0.500 g, 3.286) was added and the mixture was cooled to 0° C. N-[(1H-1,2,3-Benzotriazol-1-yloxy)(dimethylamino)methylene]-N-methylmethanaminium tetrafluoroborate (1.161 g, 3.615 mmol) and N-ethyl-N,N-diisopropylamine (0.892 g, 6.901 mmol) were added. The solution was stirred overnight at room temperature. EtOAc (20 ml) was added and the organic phase was washed with two portions of Na$_2$CO3 (2×20 ml, aq). The organic layer was dried (MgSO$_4$) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried (MgSO$_4$) and the solvent was removed by evaporation to give 0.69 g of N-ethyl-N-(2-fluorobenzyl)-2-(4-hydroxyphenyl)acetamide (yield 73.1%).

$^1$HNMR (Rotamers, 500 MHz, CDCl$_3$): δ 1.12 (m, 3H), 3.35-3.5 (m, 2H), 3.62-3.72 (m, 2H), 4.57-4.78 (m, 2H), 6.7 (t, 2H), 6.98-7.38 (m, 6H).

b) N-Ethyl-N-(2-fluorobenzyl)-2-(4-hydroxyphenyl)acetamide (0.381 g, 1.327 mmol) and methyl 2-(bromomethyl)benzoate (0.334 g, 1.460 mmol) were dissolved in acetonitrile (10 ml) and potassium carbonate (0.367 g, 2.654 mmol) was added. The mixture was stirred at 65° C. for three hours. When N-ethyl-N-(2-fluorobenzyl)-2-(4-hydroxyphenyl)acetamide was consumed, PS-trisamine (0.3 eqv) was added and the solution was stirred overnight at room temperature. The polymer was filtered off and acetonitrile was removed by evaporation. EtOAc (10 ml) was added and the organic phase was washed with two portions of water, dried (MgSO$_4$) and the solvent was removed by evaporation to give 0.545 g of methyl 2-[(4-{2-[ethyl(2-fluorobenzyl)amino]-2-oxoethyl}phenoxy)methyl]benzoate (yield 94.3%).

$^1$HNMR (Rotamers, 300 MHz, CDCl$_3$): δ 1.12 (m, 3H), 3.23-3.35 (m, 2H), 3.6-3.75 (m, 2H), 3.88 (s, 3H), 4.45-4.70 (m, 2H), 5.45 (s, 2H), 6.84-7.35 (m, 9H), 7.5 (t, 1H), 7.72 (d, 1H), 8.0 (d, 1H).

c) Methyl 2-[(4-{2-[ethyl(2-fluorobenzyl)amino]-2-oxoethyl}phenoxy)methyl]-benzoate (0.545 g, 1.251 mmol) was dissolved in EtOH (5 ml) and potassium hydroxide (0.105 g, 1.877 mmol) was added. The reaction was performed in a single node microwave oven (7 min, 150° C.). Workup was by removing the solvent by evaporation, addition of HCl (20 ml, 1 M) and the water phase was washed with two portions of EtOAc (20 ml). The organic phases were pooled and the solvent was removed by evaporation. The crude was purified by preparative HPLC (starting with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried (MgSO$_4$). The solvent was removed by evaporation to give 0.124 g of 2-[(4-{2-[ethyl(2-fluorobenzyl)amino]-2-oxoethyl}phenoxy)methyl]benzoic acid (23.5%).

$^1$HNMR (Rotamers, 500 MHz, CDCl$_3$): δ 1.12 (m, 3H), 3.25-3.5 (m, 2H), 3.65-3.8 (m, 2H), 4.5-4.75 (m, 2H), 5.52 (m, 2H), 6.84-7.45 (m, 9H), 7.55 (t, 1H), 7.78 (d, 1H), 8.13 (d, 1H).

Example 13

2-[(4-{3-[Ethyl(2-fluorobenzyl)amino]-3-oxopropyl}phenoxy)methyl]benzoic acid a) N-(2-Fluorobenzyl)ethanamine (0.554 g, 3.615 mmol) was dissolved in DMF (10 ml). 3-(4-hydroxyphenyl)propanoic acid (0.546 g, 3.286 mmol) was added and the mixture was cooled to 0° C. N-[(1H-1,2,3-benzotriazol-1-yloxy)(dimethylamino)-methylene]-N-methylmethanaminium tetrafluoroborate (1.161 g, 3.615 mmol) and N-ethyl-N,N-diisopropylamine (0.892 g, 6.901 mmol) was added. The solution was stirred overnight at room temperature. EtOAc (20 ml) was added and the organic phase was washed with two portions of Na$_2$CO$_3$ (2×20 ml, aq). The organic layer was dried (MgSO$_4$) and the solvent was removed by evaporation. The crude was purified by preparative HPLC (starting with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried (MgSO4) and then solvent was removed by evaporation to give 0.803 g of N-ethyl-N-(2-fluorobenzyl)-3-(4-hydroxyphenyl)propanamide (yield 81.1%).

$^1$HNMR (Rotamers, 500 M, CDCl$_3$): δ 1.1 (m, 3H), 2.58-2.72 (m, 2H), 2.83-3.0 (m, 2H), 3.2-3.5 (m, 2H), 4.45-4.7 (m, 2H), 6.78 (t, 2H), 6.95-7.35 (m, 6H).

b) N-Ethyl-N-(2-fluorobenzyl)-3-(4-hydroxyphenyl)propanamide (0.400 g, 1.327 mmol) and methyl 2-(bromomethyl)benzoate (0.334 g, 1.460 mmol) were dissolved in acetonitrile (10 ml) and potassium carbonate (0.367 g, 2.654 mmol) was added. The mixture was stirred at 65° C. for three hours. When N-ethyl-N-(2-fluorobenzyl)-2-(4-hydroxyphenyl)acetamide was consumed, PS-trisamine (0.3 eqv) was added and the solution was stirred overnight at room temperature. The polymer was filtered off and acetonitrile was removed by evaporation. EtOAc (10 ml) was added and the organic phase was washed with two portions of water, dried (MgSO$_4$) and the solvent was removed by evaporation. EtOAc (10 ml) was added and the organic phase was washed with two portions on water, dried (MgSO$_4$) and the solvent was removed by evaporation. The crude was purified by preparative HPLC (starting with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried (MgSO$_4$). The solvent was removed by evaporation. to give 0.454 g of methyl 2-[(4-{3-[ethyl(2-fluorobenzyl)amino]-3-oxopropyl}phenoxy)methyl]-benzoate (yield 76.1%).

$^1$HNMR (Rotamers, 400 MHz, CDCl$_3$): δ 1.08 (m, 3H), 2.52-2.68 (m, 2H), 2.9-3.03 (m, 2H), 3.18-3.45 (m, 2H), 3.88 (s, 3H), 4.454.7 (m, 2H), 5.45 (s, 2H), 6.82-7.28 (m, 8H), 7.36 (t, 1H), 7.53 (t, 1H), 7.73 (d, 1H), 8.0 (d, 1H).

c) Methyl 2-[(4-{3-[ethyl(2-fluorobenzyl)amino]-3-oxopropyl}phenoxy)methyl]-benzoate (0.454 g, 1.001 mmol) was dissolved in EtOH (5 ml) and potassium hydroxide (0.085 g, 1.514 mmol) was added. The reaction was performed in a single node microwave oven (7 min, 150° C.). Workup was by removing the solvent by evaporation, addition of HCl (20 ml, 1 M) and the water phase was washed with two portions of EtOAc (20 ml). The organic phases were pooled and the solvent was removed by evaporation. The crude was purified by preparative HPLC (starting with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried ($MgSO_4$). The solvent was removed by evaporation to give 0.079 g of 2-[(4-{3-[ethyl (2-fluorobenzyl)amino]-3-oxopropyl}phenoxy)methyl]benzoic acid (18.0%).

$^1$HNMR (Rotamers, 500 MHz, $CDCl_3$): δ 1.12 (m, 3H), 2.60-2.75 (m, 2H), 3.03 (m, 2H), 3.23-3.50 (m, 2H), 4.45-4.73 (m, 2H), 5.57 (s, 2H), 6.88-7.35 (m, 8H), 7.41 (t, 1H), 7.60 (t, 1H), 7.80 (d, 1H), 8.18 (d, 1H).

The following Examples were prepared in a similar manner.

Example 14

2-{[(3-{2-[(2,4-Difluorobenzyl)(heptyl)amino]-2-oxoethyl}phenyl)thio]methyl}benzoic acid Example 15

2-{[(4-{2-[(4-Chlorobenzyl)(ethyl)amino]-2-oxoethyl}phenyl)thio]methyl}benzoic acid Biological Activity Formulations Compounds were dissolved in DMSO to obtain 16 mM stock solutions. Before assays, stock solutions were further diluted in DMSO and culture media.

General Chemicals and Reagents

Luciferase assay reagent was purchased from Packard, USA. Restriction Enzymes were from Boehringer and Vent polymerase from New England Biolabs.

Cell Lines and Cell Culture Conditions

U2-OS, (Osteogenic sarcoma, Human) was purchased from ATCC, USA. Cells were expanded and refrozen in batches from passage number six. Cells were cultured in Dulbecco's modified Eagle medium (DMEM) with 25 mM glucose, 2 mM glutamine or 4 mM L-alanyl-L-glutamine, 10% fetal calf serum, at 5% $CO_2$. Phosphate buffered saline (PBS) without addition of calcium or magnesium was used. All cell culture reagents were from Gibco (USA) and 96-well cell culture plates were purchased from Wallach.

Plasmid Constructs for Heterologous Expression

Standard recombinant DNA techniques were carried out as described by Ausubel (7). The Luciferase reporter vector, pGL5UAS (clone consists of five copies of the GAL4 DNA binding sequence, 5'-CGACGGAGTACTGTCCTC-CGAGCT-3', cloned into the SacI/XhoI sites of pGL3-Promoter (Promega). The SacI/XhoI fragment carrying the UAS sites was constructed using annealed overlapping oligonucleotides.

Expression vectors used are based upon pSG5 (Stratagene). All vectors contain an EcoRI/NheI fragment encoding the DNA binding domain of GAL4 (encoding amino acid positions 1-145 of database accession number P04386) followed by an in-frame fusion to a fragment encoding the nuclear localisation sequence from T antigen of Polyoma Virus. The nuclear localisation sequence was constructed using annealed overlapping oligonucleotides creating NheI/KpnI sticky ends (5'-CTAGCGCTCCTAGAAGAAACG-CAAGGTTGGTAC-3'). The ligand binding domains from human and mouse PPARα and human and mouse PPARγ were PCR amplified as KpnI/BamHI fragments and cloned in frame to the GAL4 DNA binding domain and the nuclear localisation sequence. The sequence of all plasmid constructs used were confirmed by sequencing.

The following expression vectors were used for transient transfections:

| vector | encoded PPAR subtype | sequence reference[1] |
|---|---|---|
| pSGGALhPPa | human PPARα | S74349, nt 625-1530 |
| pSGGALmPPa | murine PPARα | X57638, nt 668-1573 |
| pSGGALhPPg | human PPARγ | U63415, nt 613-1518 |
| pSGGALmPPg | murine PPARγ | U09138, nt 652-1577 |

[1] refers to nucleotide positions of data base entry used to express the ligand binding domain.

Transient Transfections

Frozen stocks of cells from passage number six were thawed and expanded to passage number eight before transfections. Confluent cells were trypsinised, washed and pelleted by centrifugation at 270×g for 2 minutes. The cell pellet was resuspended in cold PBS to a cell concentration of about 18×10$^6$ cells/ml. After addition of DNA, the cell suspension was incubated on ice for approximately 5 minutes before electroporation at 230 V, 960 µF in Biorad's Gene Pulser™ in 0.5 ml batches. A total of 50 µg DNA was added to each batch of 0.5 ml cells, including 2.5 µg expression vector, 25 µg reporter vector and 22.5 µg unspecific DNA (pBluescript, Stratagene).

After electroporation, cells were diluted to a concentration of 320'000 cells/ml in DMEM without phenol red, and approximately 25'000 cells/well were seeded in 96-well plates. In order to allow cells to recover, seeded plates were incubated at 37° C. for 3-4 hours before addition of test compounds. In assays for PPARα, the cell medium was supplemented with resin-charcoal stripped fetal calf serum (FCS) in order to avoid background activation by fatty acid components of the FCS. The resin-charcoal stripped FCS was produced as follows; for 500 ml of heat-inactivated FCS, 10 g charcoal and 25 g Bio-Rad Analytical Grade Anion Exchange Resin 200-400 mesh were added, and the solution was kept on a magnetic stirrer at room temperature over night. The following day, the FCS was centrifuged and the stripping procedure was repeated for 4-6 hours. After the second treatment, the FCS was centrifuged and filter sterilised in order to remove remnants of charcoal and resin.

Assay Procedure

Stock solutions of compounds in DMSO were diluted in appropriate concentration ranges in master plates. From master plates, compounds were diluted in culture media to obtain test compound solutions for final doses.

After adjustment of the amount of cell medium to 75 µl in each well, 50 µl test compound solution was added. Transiently transfected cells were exposed to compounds for about 24 hours before the luciferase detection assay was performed. For luciferase assays, 100 µl of assay reagent was added manually to each well and plates were left for approximately 20 minutes in order to allow lysis of the cells.

After lysis, luciferase activity was measured in a 1420 Multiwell counter, Victor, from Wallach.

Reference Compounds

The TZD pioglitazone was used as reference substance for activation of both human and murine PPARγ. 5,8,11,14-Eicosatetrayonic acid (ETYA) was used as reference substance for human PPARα.

Calculations and Analysis

For calculation of $EC_{50}$ values, a concentration-effect curve was established. Values used were derived from the average of two or three independent measurements (after subtraction of the background average value) and were expressed as the percentage of the maximal activation obtained by the reference compound. Values were plotted against the logarithm of the test compound concentration. $EC_{50}$ values were estimated by linear intercalation between the data points and calculating the concentration required to achieve 50% of the maximal activation obtained by the reference compound.

The compounds of formula I have an $EC_{50}$ of less than 50 μmol/l for PPARα and preferred compounds have an $EC_{50}$ of less than 5 μmol/l. For example the $EC_{50}$s of some of the Examples for human PPAR alpha are:

| | |
|---|---|
| Example 5 | 0.163 μmol/l; |
| Example 10 | 0.168 μmol/l; |
| Example 11 | 0.026 μmol/l; and |
| Example 15 | 0.027 μmol/l. |

The invention claimed is:

1. A compound of formula I

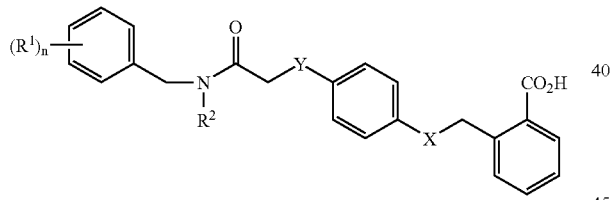

I wherein
n is 0, 1 or 2 and
$R^1$ represents halo, a $C_{1-4}$alkyl group which is optionally substituted by one or more fluoro, a $C_{1-4}$alkoxy group which is optionally substituted by one or more fluoro and wherein when n is 2 the substituents $R^1$ may be the same or different;
$R^2$ represents a $C_{2-8}$alkyl group which is optionally interrupted by oxygen;
Y is absent or represents methylene; and
X is O or S;
or a pharmaceutically acceptable salt or prodrug thereof.

2. A compound according to claim 1 in which X is O.

3. A compound according to claim 1 in which X is S.

4. A compound according to claim 1 in which Y is methylene.

5. A compound according to claim 1 in which Y is absent.

6. A compound according to claim 1 in which $R^1$ is halo, a $C_{1-4}$alkyl group or a $C_{1-4}$alkoxy group and n is 1 or 2.

7. A compound according to claim 1 in which $R^1$ is fluoro, methoxy, or isopropyl when n is 1 or 2.

8. A compound according to claim 1 in which n is 0.

9. A compound according to claim 1 in which $R^2$ represents a $C_{5-7}$alkyl group.

10. A compound selected from:
2-[(4-{3-[benzyl(hexyl)amino]-3-oxopropyl}phenoxy)methyl]benzoic acid;
2-{[(4-{2-[(2,4-difluorobenzyl)(heptyl)amino]-2-oxoethyl}phenyl)thio]methyl}benzoic acid;
2-[(4-{2-[benzyl(hexyl)amino]-2-oxoethyl}phenoxy)methyl]benzoic acid;
2-[(4-{2-[(2,4-difluorobenzyl)(heptyl)amino]-2-oxoethyl}phenoxy)methyl]benzoic acid;
2-[(4-{3-[(2,4-difluorobenzyl)(heptyl)amino]-3-oxopropyl}phenoxy)methyl]benzoic acid;
2-{[(4-{3-[(2,4-difluorobenzyl)(heptyl)amino]-3-oxopropyl}phenyl)thio]methyl}benzoic acid;
2-[(4-{3-[butyl(2,3-dimethoxybenzyl)amino]-3-oxopropyl}phenoxy)methyl]benzoic acid;
2-[(4-{3-[(2,3-dimethoxybenzyl)(heptyl)-amino]-3-oxopropyl}phenoxy)methyl]benzoic acid;
2-[(4-{3-[(3-ethoxypropyl)(4-isopropylbenzyl)amino]-3-oxopropyl}phenoxy)methyl]-benzoic acid;
2-[(4-{3-[(2,4-difluorobenzyl)(propyl)amino]-3-oxopropyl}phenoxy)methyl]benzoic acid;
2-[(4-{2-[ethyl(2-fluorobenzyl)amino]-2-oxoethyl}phenoxy)methyl]benzoic acid;
2-[(4-{3-[ethyl(2-fluorobenzyl)amino]-3-oxopropyl}phenoxy)methyl]benzoic acid;
2-({[4-(2-{ethyl[4-(trifluoromethyl)benzyl]amino}-2-oxoethyl)phenyl]thio}-methyl)benzoic acid;
2-{[(3-{2-[(2,4-difluorobenzyl)(heptyl)amino]-2-oxoethyl}phenyl)thio]methyl}benzoic acid; and
2-{[(4-{2-[(4-chlorobenzyl)(ethyl)amino]-2-oxoethyl}phenyl)thio]methyl}benzoic acid or a pharmaceutically acceptable salt thereof.

11. A compound according to claim 2 selected from:
2-[(4-{3-[benzyl(hexyl)amino]-3-oxopropyl}phenoxy)methyl]benzoic acid;
2-[(4-{2-[benzyl(hexyl)amino]-2-oxoethyl}phenoxy)methyl]benzoic acid;
2-[(4-{2-[(2,4-difluorobenzyl)(heptyl)amino]-2-oxoethyl}phenoxy)methyl]benzoic acid;
2-[(4-{3-[(2,4-difluorobenzyl)(heptyl)amino]-3-oxopropyl}phenoxy)methyl]benzoic acid;
2-[(4-{3-[butyl(2,3-dimethoxybenzyl)amino]-3-oxopropyl}phenoxy)methyl]benzoic acid;
2-[(4-{3-[(2,3-dimethoxybenzyl)(heptyl)-amino]-3-oxopropyl}phenoxy)methyl]benzoic acid;
2-[(4-{3-[(3-ethoxypropyl)(4-isopropylbenzyl)amino]-3-oxopropyl}phenoxy)methyl]-benzoic acid;
2-[(4-{3-[(2,4-difluorobenzyl)(propyl)amino]-3-oxopropyl}phenoxy)methyl]benzoic acid;
2-[(4-{2-[ethyl(2-fluorobenzyl)amino]-2-oxoethyl}phenoxy)methyl]benzoic acid; and
2-[(4-{3-[ethyl(2-fluorobenzyl)amino]-3-oxopropyl}phenoxy)methyl]benzoic acid;
or a pharmaceutically acceptable salt thereof.

12. A compound according to claim 3 which is:
2-{[(4-{2-[(2,4-difluorobenzyl)(heptyl)amino]-2-oxoethyl}phenyl)thio]methyl}benzoic acid or a pharmaceutically acceptable salt thereof.

13. A pharmaceutical formulation comprising a compound according to claim 1 or claim 10 in admixture with pharmaceutically acceptable adjuvants, diluents and/or carriers.

14. A method of treating or preventing insulin resistance comprising the administration of a compound according to claim 1 or claim 10 to a mammal in need thereof.

15. A process to prepare a compound of formula I as defined in claim 1 comprising reacting a compound of formula II

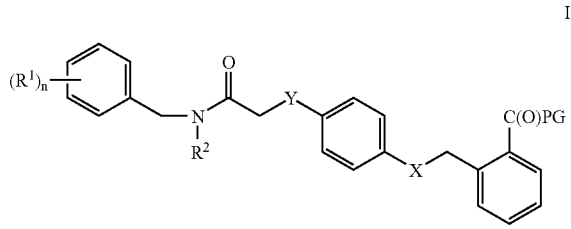

in which $R^1$, n, $R^2$, X and Y are as defined in claim 1 and PG represents a protecting group for a carboxylic hydroxy group with a de-protecting agent.

16. A compound of formula II as described in claim 15.

17. A combination treatment comprising a compound according to claim 1 or claim 10 in combination with another therapeutic agent that is useful in the treatment of disorders associated with the development and progress of atherosclerosis, hypertension, hyperlipidaemias, dyslipidaemias, diabetes and obesity.

18. A compound according to claim 4 in which $R^1$ is halo, a $C_{1-4}$alkyl group or a $C_{1-4}$alkoxy group and n is 1 or 2.

19. A compound according to claim 5 in which $R^1$ is halo, a $C_{1-4}$alkyl group or a $C_{1-4}$alkoxy group and n is 1 or 2.

20. A compound according to claim 4 in which $R^1$ is fluoro, methoxy, or isopropyl when n is 1 or 2.

21. A compound according to claim 5 in which $R^1$ is fluoro, methoxy, or isopropyl when n is 1 or 2.

22. A compound according to claim 4 in which n is 0.

23. A compound according to claim 5 in which n is 0.

24. A compound according to claim 3 which is:
2-{[(4-{3-[(2,4-difluorobenzyl)(heptyl)amino]-3-oxopropyl}phenyl)thio]methyl}benzoic acid or a pharmaceutically acceptable salt thereof.

25. A compound according to claim 3 which is:
2-({[4-(2-{ethyl[4-(trifluoromethyl)benzyl]amino}-2-oxoethyl)phenyl]thio}-methyl)benzoic acid or a pharmaceutically acceptable salt thereof.

26. A compound according to claim 3 which is:
2-{[(3-{2-[(2,4-difluorobenzyl)(heptyl)amino]-2-oxoethyl}phenyl)thio]methyl}benzoic acid or a pharmaceutically acceptable salt thereof.

27. A compound according to claim 3 which is:
2-{[(4-{2-[(4-chlorobenzyl)(ethyl)amino]-2-oxoethyl}phenyl)thio]methyl}benzoic acid or a pharmaceutically acceptable salt thereof.

* * * * *